United States Patent
Hofvander et al.

(10) Patent No.: US 11,905,343 B2
(45) Date of Patent: Feb. 20, 2024

(54) AMYLOPECTIN POTATO STARCH WITH IMPROVED STABILITY AGAINST RETROGRADATION AND IMPROVED FREEZE AND THAW STABILITY

(71) Applicant: Sveriges Starkelseproducenter, forening u.p.a., Fjalkinge (SE)

(72) Inventors: Per Hofvander, Bjärred (SE); Mariette Andersson, Lund (SE); Mathias Samuelsson, Kristianstad (SE); Åke Ståhl, Sösdala (SE)

(73) Assignee: SVERIGES STARKELSEPRODUCENTER, FORENING U.P.A., Fjalkinge (SE)

( * ) Notice: Subject to any disclaimer, the term of this patent is extended or adjusted under 35 U.S.C. 154(b) by 991 days.

(21) Appl. No.: 16/098,584

(22) PCT Filed: May 3, 2017

(86) PCT No.: PCT/SE2017/050429
§ 371 (c)(1),
(2) Date: Nov. 2, 2018

(87) PCT Pub. No.: WO2017/192095
PCT Pub. Date: Nov. 9, 2017

(65) Prior Publication Data
US 2019/0135946 A1    May 9, 2019

(30) Foreign Application Priority Data
May 3, 2016 (SE) .................................. 1650598-4

(51) Int. Cl.
| | |
|---|---|
| C08B 30/12 | (2006.01) |
| C08B 30/20 | (2006.01) |
| C12N 15/82 | (2006.01) |
| C08L 3/12 | (2006.01) |
| C08L 3/02 | (2006.01) |
| C12N 15/90 | (2006.01) |

(52) U.S. Cl.
CPC .............. *C08B 30/12* (2013.01); *C08B 30/20* (2013.01); *C08L 3/02* (2013.01); *C08L 3/12* (2013.01); *C12N 15/8213* (2013.01); *C12N 15/8245* (2013.01); *C12N 15/90* (2013.01)

(58) Field of Classification Search
None
See application file for complete search history.

(56) References Cited

U.S. PATENT DOCUMENTS

| | | | |
|---|---|---|---|
| 6,589,293 B1 * | 7/2003 | Guns ...................... | A61K 8/732 8/94.1 R |
| 6,600,093 B1 | 7/2003 | Visser et al. | |
| 8,148,517 B2 * | 4/2012 | Soyka .................... | C12N 9/107 435/97 |
| 2006/0216402 A1 | 9/2006 | Klucinec et al. | |

FOREIGN PATENT DOCUMENTS

| | | |
|---|---|---|
| WO | WO-92/11376 A1 | 7/1992 |
| WO | WO-0119975 A2 | 3/2001 |
| WO | WO-2005123927 A1 | 12/2005 |

(Continued)

OTHER PUBLICATIONS

Jens et al., "Understanding and Influencing Starch Biochemistry", Critical Reviews in Plant Sciences, vol. 19, Issue No. 3, pp. 171-226, 2000.

(Continued)

*Primary Examiner* — Brent T Page
(74) *Attorney, Agent, or Firm* — MOSER TABOADA

(57) ABSTRACT

Amylopectin potato starch with improved stability against retrogradation and improved freeze and thaw stability, wherein it contains more than 99% amylopectin, preferably 100% amylopectin, is disclosed, as well as a method for the production of a potato (*Solanum tuberosum*) containing said amylopectin potato starch, wherein said method involves homology-directed mutagenesis using CRISPR/nuclease technology and comprises the following steps:

a) provision of potato cells or potato tissue containing potato cells, b) introduction into the nuclei of said potato cells of one or more CRISPR/nuclease complexes each comprising a specific targeting ribonucleotide sequence which is fully or essentially homologous to a target nucleotide sequence located in a DNA sequence immediately upstream of a PAM (5'-NGG-3'protospacer adjacent motif) in a gene coding for a GBSS enzyme and optionally also in a gene coding for an SSII enzyme and/or in a gene coding for an SSIII enzyme, wherein said mutagenesis takes place in one or more alleles of the potato genome, wherein when said targeting ribonucleotide sequence identifies the complementary strand of the target nucleotide sequence, said one or more CRISPR/nuclease complexes cut(s) said DNA sequence, leading to a subsequent complete lack of the ability of the potato to produce a functional GBSSI enzyme, optionally also a functional SSII and/or SSIII enzyme, c) wherein step b) optionally is repeated until the potato lacks the ability to produce said functional GBSSI enzyme, optionally also a functional SSII and/or SSIII enzyme, in all of the alleles, preferably 3 times, a potato obtained by said method, a method for the production of said amylopectin potato starch from said potato, and different uses of said amylopectin potato starch.

11 Claims, 12 Drawing Sheets

Specification includes a Sequence Listing.

(56) References Cited

FOREIGN PATENT DOCUMENTS

| WO | WO-2006/103107 A1 | 10/2006 |
|----|-------------------|---------|
| WO | WO-2008090008 A1 | 7/2008 |
| WO | WO-2011/054729 A2 | 5/2011 |
| WO | WO2014/194190 A1 | 12/2014 |
| WO | WO-2015193858 A1 | 12/2015 |
| WO | WO-2017192095 A1 | 11/2017 |

OTHER PUBLICATIONS

Yan et al., "Study On Physicochemical Characteristics of Waxy Potato Starch in Comparison With Other Waxy Starches", Starch, vol. 63, pp. 754-759, 2011.

Xie et al., "Effect of Repeated Retrogradation on Structural Characteristics and in Vitro Digestibility of Waxy Potato Starch", Food Chemistry, vol. 163, pp. 219-225, 2014.

Belhaj et al., "Editing Plant Genomes With CRISPR/CAS9", Current Opinion in Biotechnology, vol. 32, pp. 76-84, 2015.

Andersson et al., "Efficient Targeted Multiallelic Mutagenesis in Tetraploid Potato (Solanum tuberosum) By Transient CRISPR-CAS9 Expression in Protoplasts", Plant Cell Reports, vol. 36, Issue No. 1, pp. 117-128, Jan. 2017.

Khlestkin V.K. et al., "Target Genes for Development of Potato (Solanum tuberosum L.) Cultivars With Desired Starch Properties (Review)", Agricultural Biology, vol. 52, No. 1, pp. 25-36, Jan. 2017.

International Search Report dated Jul. 5, 2017 for PCT Application No. PCT/SE2017/050429.

European Search Report for Application No. 17792956.9-1118, dated Jul. 4, 2022, 8 pages.

Schlussbericht, Züchterische Optimierung von Spezialstärken, Bioplant-Biotechnologisches Forschungslabor GmbH, Gefördert durch: Bundesministerium für Ernährung, Landwirtschaft und Verbraucherschutz, 29 pages.

Hovenkamp-Hermelink et al., "Isolation of an Amylose-Free Starch Mutant of the Potato (Solanum tuberosum L.)". Theoretical and Applied Genetics; International Journal of Plant Breeding Research, Springer, Berlin, DE, vol. 75, No. 1, pp. 217-221, XP000610709, Dec. 1, 1987.

Bruinenberg et al., "The Potato as an Industrial Raw Material: Market Evolution, New Products, Technological and Biotechnological Aspects", Conference Triennale De L'Association Europeenne Pour Larecherche Sur La Pomme De Terre, pp. 85-94, XP000560811, Jan. 1, 1994.

Jobling et al., "Production of a freeze-thaw-stable potato starch by antisense inhibition of three starch synthase genes", Nature Biotechnology, Gale Group Inc, New York, vol. 20, No. 3, pp. 295-299, XP002346240, Mar. 1, 2002.

Fulton et al., "Role of Granule-bound Starch Synthase in Determination of Amylopectin Structure and Starch Granule Morphology in Potato", Journal of Biological Chemistry, vol. 277, No. 13, pp. 10834-10841, XP055471255, Mar. 29, 2002.

Steve Jobling, "Improving starch for food and industrial applications", Current Opinion in Plant Biology, Quadrant Subscription Services, GB, vol. 7, No. 2, pp. 210-218, XP002352216, Apr. 1, 2004.

Anonymous., "New Potato Starch Possibilities", XP05551033, URL:https://www.foodingredientsfirst.com/news/new-potato-starch-possibilities.html, Oct. 3, 2005.

Supplementary Partial European Search Report on Application No. 17792956.9, dated Nov. 19, 2019.

Wang, et al., "Efficient targeted mutagenesis in potato by the CRISPR/Cas9 system", Plant Cell Rep (2015) 34:1473-1476; Published online Jun. 17, 2015.

"Breeding optimization of special strengths"; Final Report; Bundesministerium für Ernährung, Landwirtschaft und aulgrund des Deutschen.

Nilsson, et al., "Determination of the Degree of Branching in Normal and Amylopectin Type Potato Starch with $^1$H-NMR Spectroscopy", Starch/Stärke 48 (1996) Nr. 10. S. 352-357.

* cited by examiner

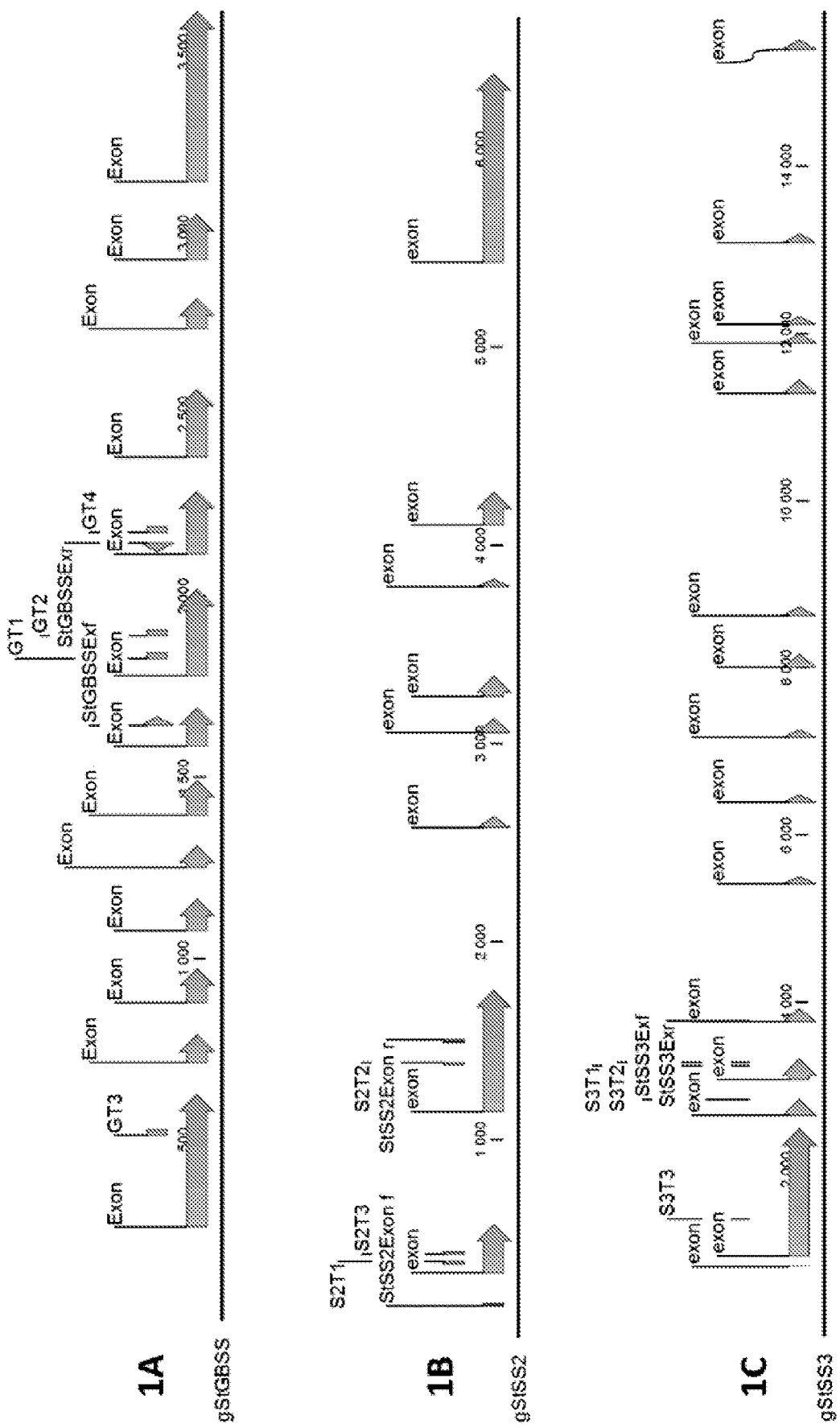
Fig. 1A-C

GT1

| ID | Sequence | Indels |
|---|---|---|
| P1003 | GGGATATTAGAATCACAT-GGGTGGTTACAGTGAGCCC | -1 |
| P1004 | GGGATATTAGAAT------GGGTGGTTACAGTGAGCCC | -6 |
| P1004 | GGGATATTAGAATCACAT-GGGTGGTTACAGTGAGCCC | -1 |
| P1030 | GGGATATTAGAA-------GGGTGGTTACAGTGAGCCC | -7 |
| P1043 | GGGATATTAGAATCA----GGGTGGTTACAGTGAGCCC | -4 |
| P1046 | GGGATATTAGAATC-----GGGTGGTTACAGTGAGCCC | -5 |
| P1071 | GGGATATTAGAATCACAT-GGGTGGTTACAGTGAGCCC | -1 |
| P1071 | GGGATATTAGAATCACA--GGGTGGTTACAGTGAGCCC | -2 |
| P2046 | GGGATATTA----------GGGTGGTTACAGTGAGCCC | -10 |
| P2058 | GGGATATTAGAATCA---AGGGTGGTTACAGTGAGCCC | -3 |
| P2096 | GGGATATTAGAATCACAT-GGGTGGTTACAGTGAGCCC | -1 |
| P5023 | GGGATATTAGAATCACAT-GGGTGGTTACAGTGAGCCC | -1 |
| P5046 | GGGATATTAGAATCACAT-GGGTGGTTACAGTGAGCCC | -1 |
| P5055 | GGGATATTAGAATCACAT-GGGTGGTTACAGTGAGCCC | -1 |
| P5059 | GGGATATTAGAATCACAT-GGGTGGTTACAGTGAGCCC | -1 |
| WT | GGGATATTAGAATCACATAGGGTGGTTACAGTGAGCCC | SEQ. ID. NO. 31 |

GT2

| ID | Sequence | Indels |
|---|---|---|
| P7021 | TTGTCTCTGCTGTTGACAAGGGT-----AATTGGACAGTGTCC | -4 |
| P7021 | TTGTCTCTGCTGTTGACAAGGGTGTTGAAATTGGACAGTGTCC | +1 |
| P7021 | TTGTCTCTGCTGTTGACAAGGGTG---ATTGGACAGTGTCC | -3 |
| P7033 | TTGTCTCTGCTGTTGACAAGGGTGTT-AATTGGACAGTGTCC | -1 |
| P7061 | TTGTCTCTGCTGTTGACAAGGGTGTT-AATTGGACAGTGTCC | -1 |
| P8006 | TTGTCTCTGCTGTTGACAAGGGTGTTG—TTGGACAGTGTCC | -2 |
| P8018 | TTGTCTCTGCTGTTGACAA---------AATTGGACAGTGTCC | -8 |
| WT | TTGTCTCTGCTGTTGACAAGGGTGTTGAATTGGACAGTGTCC | SEQ. ID. NO. 32 |

GT3

| ID | Sequence | Indels |
|---|---|---|
| P9064 | CTGGATGCTCAGCTACCATTGTTT--AAAGGGAATGAACTTGAT | -2 |
| WT | CTGGATGCTCAGCTACCATTGTTTGTAAAGGGAATGAACTTGAT | SEQ. ID. NO. 33 |

| ID | Sequence | Indels |
|---|---|---|
| P10019 | CCTGTTGACAAGAAGATCCCT--GATTGGCTTCATCGG | -2 |
| P10023 | CCTGTTGACAAGAAGATCCCTTTAGATTGGCTTCATCGG | +1 |
| P10025 | CCTGTTGACAAGAAG--------GATTGGCTTCATCGG | -8 |
| P10025 | CCTGTTGACAAGAAGATCC----GATTGGCTTCATCGG | -4 |
| P10031 | CCTGTTGACAAGAAGATCCCTTTTGATTGGCTTCATCGG | +1 |
| P10031 | CCTGTTGACAAGAA---------GATTGGCTTCATCGG | -9 |
| P10084 | CCTGTTGACAAGAAGATCCCT--GATTGGCTTCATCGG | -2 |
| P10084 | CCTGTTGACAAGAAGATCC--------CTTCATCGG | -8 |
| P10087 | CCTGTTGACAAGAAGATCCCT--GATTGGCTTCATCGG | -2 |
| P11088 | CCTGTT----------------GATTGGCTTCATCGG | -17 |
| P11088 | CCTGTTGACAAGAAGATCCCT---ATTGGCTTCATCGG | -3 |
| P11088 | CCTGTTGACAAGAAGATCCCTTTTGATTGGCTTCATCGG | +1 |
| WT | CCTGTTGACAAGAAGATCCCTTTGAT<u>TGG</u>CTTCATCGG | SEQ. ID. NO. 34 |

S2T1

| ID | Sequence | Indels |
|---|---|---|
| P19022 | TTTTGGGCCTAAGTGCTAAAAGGGGTA--TTGGGGTGG | -2 |
| P19022 | TTTTGGGCCTAAGTGCTAAAAGGGGTAA-TTGGGGTGG | -1 |
| P19022 | TTTTGGGCCTAAGTGCTAAAAGGGGTAAGTTTGGGGTGG | +1 |
| P19026 | TTTTGGGCCTAAGTGCTAAAAGGGGT---TTGGGGTGG | -3 |
| WT | TTTTGGGCCTAAGTGCTAAAAGGGGTAGTT<u>GGG</u>GTGG | SEQ. ID. NO. 35 |

S2T2

| ID | Sequence | Indels |
|---|---|---|
| P21011 | GGGGGTGCCCTTTCATCGTGCCAGGTCCCTTTT | +1 |
| WT | GGGGGTGCCCTTTCATCGGC<u>AGG</u>TCCCTTTT | SEQ. ID. NO. 36 |

S3T1

| ID | Sequence | Indels |
|---|---|---|
| P12019 | CAGCGATTAAATGAACATCTGAACCAA--TTCAGGTTT | -2 |
| WT | CAGCGATTAAATGAACATCTGAACCAAATTC<u>AGG</u>TTT | SEQ. ID. NO. 37 |

Fig. 5 (cont.)

S3T2                                                                            Indels

P19022  GGCGACATTTTCTGAGGTGGCAATGGAC--AGGCGGTG          -2

P21004  GGCGACATTTTCTGAGGTGGCAATG-----AGGCGGTG          -5

P21006  GGCGACATTTTCTGAGGTGGCAATGGAC--AGGCGGTG          -2

P21009  GGCGACATTTTCTGAGGTGGCAATGG----AGGCGGTG          -4

P21011  GGCGACATTTTCTGAGGTGG----------AGGCGGTG          -10

WT      GGCAACATTTTCTGAGGTGGCAATGGACCCAGGCGGTG      SEQ. ID. NO. 38

Fig. 5 (cont.)

AMYLOPECTIN POTATO STARCH WITH IMPROVED STABILITY AGAINST RETROGRADATION AND IMPROVED FREEZE AND THAW STABILITY

SEQUENCE LISTING STATEMENT

Filed herewith is a Sequence Listing (name: AWA121_Sequence_Listing.txt; created: Sep. 22, 2020; sized: 18,952 bytes). The content of that Sequence Listing is incorporated herein by reference in its entirety.

TECHNICAL FIELD OF THE INVENTION

The present invention refers to an amylopectin potato starch with improved stability against retrogradation and improved freeze and thaw stability, to a method for the production of a potato containing said amylopectin starch, to a potato containing said amylopectin starch, to a method for the production of said amylopectin potato starch, and to uses of said amylopectin potato starch.

BACKGROUND ART

Starch is one of the most used food ingredients in the world. It is primarily used as a thickening agent and thus impart viscosity and texture to food products like soups, sauces, dairy products, fruit preparation etc. It is also used for fat replacement in a large variety of food applications and for many other purposes, e.g. coating of nuts, deep fried foods and as a gelatin replacer in confectionary products, as a stabilizer of oil in water emulsions for liquid emulsions and spray dried functional oils. Starch is found in a large variety of food products in its native state or in a modified form to give the requested performance. Starch is extracted from different botanical sources, e.g. maize, potato, tapioca, wheat, barley, rice etc. and the performance of the starch depends on a number of physical and chemical properties. One of the main characteristics of the starch is the ratio of amylose and amylopectin. The polysaccharide starch is a polymer made from a chemically uniform monomer, the glucose molecule. However, it is a very complex mixture of different forms of molecules which differ with respect to their degree of polymerization and the occurrence of branching of the glucose chains. Starch is therefore not a uniform raw material. A differentiation is made in particular between amylose starch, an essentially unbranched polymer of α-1,4-glycosidically linked glucose molecules, and amylopectin starch, which for its part is a complex mixture of differently branched glucose chains. In typical plants used for starch production, such as maize, potato, wheat, barley, rice, and tapioca, the synthesized starch consists of about 20%-30% of amylose starch and 70%-30% of amylopectin starch.

For a considerable time amylose was regarded as a linear polymer, consisting of α-1,4-glycosidically linked α-D-glucose monomers. However, research has proven the presence of α-1,6-glycosidic branching points with short chains, called stubs, at the branching points. The chain length of the stubs is defined to be less than 20 DP (STARCH Metabolism and Structure, Nakamura Yasunori, Springer 2015) but other research is also indicating slightly longer stubs (Cure et al, Amylose is not Strictly Linear, Biosynthesis, Nutrition and Biomedical, Vol 47, 1995, 207-209).

Amylopectin consists of a complex mixture of variably branched glucose chains that can be differentiated into A-chains, B-chains with different lengths and C-chain. Unlike amylose, amylopectin is more highly branched. Side chains are linked to the primary chain (the C-chain, consisting of α-1,4-glycosidically linked α-D-glucose monomers) via an α-1,6-glycosidic bond. According to textbook information (Voet and Voet, Biochemistry, John Wiley & Sons, 1990), the α-1,6 branches occur on average every 24 to 30 glucose units. This corresponds to a degree of branching of approx. 3%-4%. The facts regarding the degree of branching vary and depend on the respective starch origin which gives different degrees of branching in between 3-6% of the amylopectin part of the starch in different botanical sources for the starch. Another fundamental difference between amylose and amylopectin lies in the molecular weight. Depending on the origin of the starch, amylose has a molecular weight ($M_w$) of approximately $3 \times 10^4$-$10^6$ Da, and in the case of amylopectin it is between $10^8$ and $10^9$ Da. The two macromolecules can be differentiated on the basis of their molecular weights and their different physicochemical properties. In addition to the amylose/amylopectin ratio, the functional characteristics of the starch are strongly influenced by the molecular weight, the side chain distribution pattern and the length of the side chain, the ion content, the lipid and protein content as well as the average starch granular size and its distribution profile. Examples of important functional characteristics are the solubility, the gelatinization behavior, the granule swelling behavior, the water binding capability, the viscosity and texture properties, the retrogradation property, the film forming properties, and the freeze/thaw stability etc.

A water system where the starch has been gelatinized undergoes a process which in general terms is called retrogradation. During the retrogradation process the starch-water system is reorganized and the process leads to syneresis. The starch molecules reform into new crystalline complexes and the water bound to the starch is released. As a consequence the reduced water binding capacity leads to the water being released from the starch-water system, a process called syneresis. At low concentrations this phenomenon will lead to a precipitation of the starch crystalline complexes, and at higher concentrations it leads to gel formation. This behavior is seen in the common starches on the market from maize, potato, tapioca, wheat, barley etc. This is well known by a skilled man in the art and depends on the starch properties which in nature depend on from which natural botanical source it is derived from. (See Jacobson R. et al, Cereal Chemistry, (1997), Volume 74, Number 5, Pages 511-518; Wang et al, Food Science and Food Safety (2015), Volume 14, pages 568-585, Hizukuri S. Carbohydrate research 141, 1985, 295-306; Roulet P Starch 42, 3, 1990 99-100). It has also been shown that the chain length of the amylopectin molecule influences this phenomenon (Hizukuri S, 1985, Kalichevsky M et al, Carbohydrate research 198, 1990, 49-55 and Jane. J et al Cereal Chemistry, (1999), Volume 76, Number 5, Pages 629-637) and also the amylose-amylopectin ratio (Fetches P et al Carbohydrate research 340, (2205), 2563-2568; Miles, M. et al, Carbohydrate research 135, 1985, 271-281; Miles J. Carbohydrate Research, Volume 135, (1985) Pages 271-281).

In most common starches the amylose content is 20-30% whereas in the so-called waxy types the quantity is lower and normally defined as less than 10%. As the presence of amylose in the starch it strongly influences the stability after gelatinization, a lower amount of amylose will have a high impact on the retrogradation behavior.

The starch retrogradation process is one of the most important factors when differentiating starches and their use in food applications but also in other applications as non-food. Most native starches must undergo some kind of chemical modification to inhibit the retrogradation process, and this inhibition can be achieved by chemical modification of the starch by coupling functional groups to the starch molecule via covalent bonding. The most common chemical modifications used in the starch industry are esterification and etherification. These chemical modifications prevent the retrogradation process of the starch. Etherification has the highest impact in food usage as the substituent is more bulky in size and can be made to higher substitution levels and still be classified as a food grade modified starch. It is therefore used to render the starch to become freeze/thaw-stable in water pastes. The function of different chemical modifications is well-known and most of the chemical modifications for food usage can be found in JECFA, Modified starches; 57th JECFA (2001) and are published in FNP 52 Add 9 (2001), FDA § 172.892 and in the EU food additive directive. Stabilization against retrogradation can also be achieved by alternative methods generally known as non-chemical modification methods. Retrogradation of starch solutions can be prevented by enzymatic modification. Degradation of the starch molecules with alpha-amylase has shown to increase the stability against retrogradation, and degradation with beta-amylase has shown a remarkable increase of the stability. If beta-amylase is allowed to totally degrade the amylose molecule and partly the amylopectin molecule, forming a beta-limit dextrin, the resulting starch solution will be extremely stable against retrogradation. The reason for the extreme improvement in the stability after degradation with beta-amylase is that the remaining amylopectin molecule will have a reduced chain length size, and this has proven to increase the retrogradation stability, as well as the freeze/thaw stability. However, enzymatic stabilization can only be achieved on non-granular starch and this kind of stabilization is therefore not possible to use for the granular starches. In granular starches, the starch texture is built up by hydrated and swollen but still intact granules, generally termed as gelatinized but dispersed starch granules, and is the common way starch is used in food applications. The enzymatic stabilization is also time consuming and means extra production costs making the starch products more expensive. Besides the enzymatic modifications it is also known that pyrodextrinization and alkaline roasting can be partly used to prevent the retrogradation phenomenon as well as complexing the amylose molecule with mono-diglycerides.

There are also natural varieties of starches which have a remarkable robustness against the retrogradation phenomenon due to their chemical structure. Starches with a smaller amount of amylose, generally known as waxy starches with an amylose content of less than 10% or even as low as less than 2%, can be found in nature, and these starches have a natural robustness against the retrogradation process but only to a limited level. The retrogradation will for this kind of starches be delayed compared to starches with higher amylose contents. Thus there is a clear correlation between the amylose content and retrogradation. (Sasaki T. Cereal Chemistry, (2000), Volume 77, Number 1, Pages 58-63). Further to this, it is well known that naturally occurring starches with an extremely low amylose content, i.e. less than 0.5%, and with a short chain structure of the amylopectin molecule are extremely stable against retrogradation. (Fredriksson H, et al, (1998), Carbohydrate polymers 35, 119-134; Jane J. L, et al, (1999), Cereal chemistry 76, (5), 629-637). One example of starch with an extremely low content of amylose and a short chain structure of the amylopectin which can be found on a commercial basis is the waxy barley starch, crossbred from the 0-amylose mutant line of barley, for example the varieties Cinnamon, Lisen and HB 340.

A starch with improved stability in starch pastes, after partly being gelatinized or after total gelatinization into a starch solution, is also of high interest in non-food applications as it opens up new possibilities of large varieties of products, e.g. as a functional component in production of adhesives, as a functional ingredient in paper industry, both as a wet-end starch but also for surface sizing and coating of paper, as a functional ingredient in emulsions for paper- and paint industry, as a functional ingredient in construction products, and as a functional ingredient in pharmaceutical production.

Starch retrogradation can be determined by a broad range of analytical methods including analyzing the properties of starch gels at both the macroscopic and molecular level. Many analytical methods are summarized in Karim A. et al: Food chemistry 71, (2000), 9-36. An easy method for deter-mining the stability of starch is to partly gelatinize the starch, consequently remained in a granular condition as a starch suspension of gelatinized and swollen granules, or totally disrupted into a starch solution in which there are no intact starch granules remaining in the system. The viscosity and texture properties of the starch suspension or solution are analyzed continuously after storage under different conditions which influences the retrogradation behavior. To analyze and determine the freeze/thaw stability the starch paste or solution is frozen and thawed and then centrifuged to rapidly press out liberated liquid. The released water, which is a result of syneresis due to forced retrogradation of the starch molecules, is siphoned off and weighed. The procedure is repeated systematically and the total amount of accumulated water release after each freeze/thaw cycle is measured and corresponds to the starch stability property and thus equals to its robustness against retrogradation.

The behavior of gelatinized starches upon cooling and storage, generally termed as the retrogradation behavior, is of great interest to food scientists and technologists since it strongly affects the quality, acceptability and shelf-life of starch-containing foods. Starch molecules in food pastes or gels are known to associate upon aging, leading to retrogradation which results in effects such as precipitation, gelation, and undesirable changes in texture due to the retrogradation of the starch. Based on these facts regarding retrogradation of starch pastes and its importance in food industry, it is of highest interest to develop starches which are more stable against the retrogradation phenomenon. There is a strong demand to develop starches which are robust against retrogradation without chemical modifications of the structure and thus can meet the demands of stability from these ones for starch pastes in food applications for storage in refrigerators or freezers without chemical modification of the starch.

It is known that plants can be genetically modified in such a way that they produce starches that can be differentiated from the starch in the corresponding none-genetically modified plant from which they have been manufactured on the basis of physicochemical parameters. A review of various plant species that exhibit a reduction in enzymes involved in starch biosynthesis has been described by Kossmann and Lloyd [1, 2] (2000, Critical Reviews in Plant Sciences 19(3), 171-126), and later by Zeeman et al. (2010, Annual Review of Plant Biology 61, 209-234)).

Potato plants have previously been disclosed in which the activity of the starch granule-bound starch synthase I (GBSSI; "Granule-Bound Starch Synthase I") is reduced (Hovenkamp-Hermelink et al., 1987, Theoretical and Applied Genetics 75, 217-221; Visser et al., 1991, Mol. Gen. Genet. 225, 289-296; Hergersberg, 1988, Dissertation, Universität Köln; WO 92/11376). The GBBSI is involved in the formation of amylose. Inhibition of GBSSI activity leads to synthesis of starch that almost exclusively is comprised of amylopectin. The corresponding GBSSI gene in maize plant is known by the term "waxy" and this is the reason why starches with lower contents of amylose in general terms are called waxy starches, e.g. waxy corn/maize, waxy potato, waxy wheat, waxy tapioca, waxy barley, waxy rice etc.

In US patent application 20120216316 A1 a method for reducing the activity of GBSSI is disclosed. The amylopectin content in the potato produced is described to be of at least 98% and with a phosphate content higher than 0.09%. In U.S. Pat. No. 6,940,001 B1, a method for reducing the activity of GBSSI and BE (Branching Enzyme) is disclosed which will lead to a starch with an amylose content below 10% and with an increased phosphate content.

Nevertheless, according to the disclosed methods in these patent documents the activity of GBSSI and BE is not completely eliminated, which is the reason for still having a significant level of amylose in the produced starch. Furthermore, the used technology used to achieve the decreased activity is based on a method which will lead to a potato with residual exogenous material.

Moreover, potato plants have been described in which the activity of Soluble Starch Synthase III and II (SSIII and SSII) is reduced (Abel et al., 1996, The Plant Journal 10(6), 981-991; Lloyd et al., 1999, Biochemical Journal 338, 515-521; WO 00/08184; WO 96/15248; EP-A 0779363). In comparison with starch isolated from the corresponding wild type plant, starch from such plants exhibits a shift from longer chains to shorter ones in the side chains of the amylopectin (Lloyd et al., 1999, Biochemical Journal 338, 515-521), no change in the amylose content (Abel et al., 1996, The Plant Journal 10(6), 9891-9991) and a reduced end viscosity via a RVA (Rapid-Visco-Analyzer) analysis (Abel, 1995, Dissertation, Freie Universität Berlin).

It has further been discovered that a combined reduction of SSIII and SSII in potato has much greater effect on the starch structure and behavior than was predicted by the reduction of the individual enzyme isoforms (WO 99/66050, Edwards et al, Plant Journal 17, 251-261, 1999). WO 01/19975 discloses plants in which both the GBSSI and the SSII and/or SSIII activity is reduced. Starch from genetically modified potato plants with reduced GBSSI, SSII and SSIII activity exhibits a lower amylose content, changed gelatinization and swelling properties of the starch granule, and an improved freeze/thaw stability in comparison to the starch from the wild type potato plant. The genetic modification technology used in the invention disclosed in WO 01/19975 is dependent on the stable introduction of one or several genetic devices for a continuous suppression to a larger or lesser degree of gene function. This will most often not lead to a complete suppression of the enzymatic activity of GBSSI, SSIII and SSII and therefore the achieved starch properties will still to some extent be influenced by these starch synthesizing enzymes.

In U.S. patent Ser. No. 00/806,67670 B2 a method for reducing the activity of GBSSI, SSIII and BEI is disclosed which leads to a starch which is defined as having an amylose content of below 10% and a phosphate content at the C6 position of 30-100 nmol per mg of starch (0.09-0.31% phosphorous of starch DM). Furthermore, this patent describes the starch properties as having freeze and thaw stability of at least 60%. According to the disclosed method in this patent, the activity of GBSSI, SSII and BEI is not completely eliminated, which is the reason for the starch still having a significant level of amylose and that the freeze and thaw stability is only partially affected by the achieved decreased activity of the specific enzymes. It can therefore be concluded that this patent is based on a technology which will only partially decrease the activity of the specific enzymes GBSSI, SSII, and BEI. Further to this, it can be concluded that the related technology disclosed in the patent will lead to a potato with residual exogenous material.

The effect of partially suppressing the biosynthetic activities of GBSSI, SSII, and SSIII can be found, inter alia, in Jobling et al 2002, wherein it has been shown that a starch modified by partial gene suppression of the GBSSI, SSIII, and SSII will lead to a starch with improved freeze/thaw stability. Thus, this starch has improved stability properties and consequently robustness against the retrogradation phenomenon.

WO 2015/193858 discloses a starch product from a *Solanum* plant comprising a mutation in each GBSS allele endogenous to said plant.

Kossmann J et al., "Understanding and influencing starch biochemistry", Critical Reviews in Plant Sciences, 2000, vol. 19, no. 3, pages 171-226, discloses that mutants lacking GBSS in potato synthesize amylose-free starch.

U.S. Pat. No. 6,600,093 (1) discloses genetically engineered potato plants producing essentially emylose-free starch and no detectable GBSS activity.

The method used in the above-mentioned WO 01/19975 and Jobling et al 2002 is based on stable integration of gene silencing constructs in the potato. As a consequence of this technology, the enzyme activity, e.g. of GBSSI and/or SSII etc., is not totally abolished or suppressed, and therefore the effect of proposed change will not reflect the effect on the starch properties to a 100% suppression. This means that, if for instance GBSSI is blocked or inhibited, small amounts of amylose starch will still be present in the starch component. In the case of blockage of the SSIII and SSII by genetically modification of the potato, it will not lead to a complete suppression of the chain length synthesized by these enzymes, and thus a small activity of SSIII and SSII is still present and small amounts of longer chains will be found in the starch material from such genetically modified plants.

Another drawback with the known technologies, e.g. in related patents, is that the achieved changes in the species are based on the stable introduction of genetic devices for the continuous suppression of the gene function. Thus, the continuous stable function of the introduced gene suppressing device can efficiently be affected by various external factors, such as biotic or abiotic factors, wherein the modified plant cell material will contain residual exogenous material.

To summarize, there is clearly a need for the provision of a potato starch having improved stability against retrogradation and improved freeze-thaw stability, as well a need for a method for the production of potatoes having the ability to express and produce such a potato starch without having any residual exogenous genetic material.

SUMMARY OF THE INVENTION

An object of the present invention is to fulfill the above-mentioned need. This object is reached with an amylopectin potato starch having the characteristics defined in claim 1. This object is also achieved with a method for the production of a potato containing said amylopectin starch, with a potato containing said amylopectin starch, with a method for the production of said amylopectin potato starch, and with uses of said amylopectin potato starch.

More precisely, in one aspect the present invention refers to an amylopectin potato starch with improved stability against retrogradation and improved freeze and thaw stability, wherein it contains more than 99% amylopectin, preferably 100% amylopectin.

In another aspect the present invention refers to a method for the production of a potato (*Solanum tuberosum*) containing the amylopectin potato starch according to claims 1-3, wherein said method involves homology-directed mutagenesis using CRISPR/nuclease technology and comprises the following steps:
 a) provision of potato cells or potato tissue containing potato cells,
 b) introduction into the nuclei of said potato cells of one or more CRISPR/nuclease complexes each comprising a specific targeting ribonucleotide sequence which is fully or essentially homologous to a target nucleotide sequence located in a DNA sequence immediately upstream of a PAM (5'-NGG-3'protospacer adjacent motif) in a gene coding for a GBSS enzyme and optionally also in a gene coding for an SSII enzyme and/or in a gene coding for an SSIII enzyme, wherein said mutagenesis takes place in one or more alleles of the potato genome, wherein when said targeting ribonucleotide sequence identifies the complementary strand of the target nucleotide sequence, said one or more CRISPR/nuclease complexes cut(s) said DNA sequence, leading to a subsequent complete lack of the ability of the potato to produce a functional GBSSI enzyme, optionally also a functional SSII and/or SSIII enzyme,
 c) wherein step b) optionally is repeated until the potato lacks the ability to produce said functional GBSSI enzyme, optionally also a functional SSII and/or SSIII enzyme, in all of the alleles.

In a further aspect the present invention refers to a potato obtained with the inventive method.

In still another aspect the present invention refers to a method for the production of amylopectin potato starch by extraction from said inventive potato.

In still another aspect the present invention refers to different uses of said amylopectin potato starch of said potato.

The different aspects of the present invention also appear in the independent claims, and further embodiments are disclosed in the accompanying dependent claims.

BRIEF DESCRIPTION OF THE DRAWINGS

FIG. 1 shows schematically genes of *Solanum tuberosum*, more precisely A) the GBSSI gene, B) the SSII gene, and C) the SSIII gene.

FIG. 2 shows schematically the results of the determination of allelic variation of Kuras, more precisely A), exon 8 of the GBSSI gene, B) exon 1 of the SSII gene and C) exon 3 of the SSIII gene. The following sequences appear in FIGS. 2A, 2B and 2C as follows:
 SEQ ID NO: Where found in Figures
 45 FIG. 2A: StG1_exon to StG3_exon and the consensus sequence (all equivalent sequences)
 46
FIG. 2B: StS2_exon2.seq
 49
FIG. 2B: StS2_exon4.seq
 50
FIG. 2B: consensus sequence
 51
FIG. 2C: StS2_exon
 53
FIG. 2C: StS3_exon
 54
FIG. 2C: consensus sequence

FIG. 5 shows the results of genotyping of individual alleles with induced mutations in GT1, GT2, GT3, GT4, S2T1, S2T2, S3T1, S3T2 and S3T3 target regions. The following sequences appear in FIG. 5 as follows:
 SEQ ID NO: Where found in FIGS.
 55-64 FIG. 5: P1003, P1004, P1004 ($2^{nd}$), P1030, P1043, P1046, P1071, P1071 ($2^{nd}$), P2046 and P2058 under "GT1" heading, respectively
 65 P2096, P5023, P5046, P5055, P5059 under "GT1" heading (all equivalent sequences)
 66-72
FIG. 5: P7021, P7021 ($2^{nd}$), P7021 ($3^{rd}$), P7033, P7061, P8006, and P8018 under "GT2" heading, respectively
 73-84
FIG. 5: P10019, P10023, P10025, P10025 ($2^{nd}$), P10031, P10031 ($2^{nd}$), P10084, P10084 ($2^{nd}$), P10087, P10088, P10088 ($2^{nd}$) and P10088 ($3^{rd}$) under "GT4" heading, respectively
 85
FIG. 5: P9064 under "GT3" heading
 86-89
FIG. 5: P19022, P19022 ($2^{nd}$), P19022 ($3^{rd}$) and P19026 under "S2T1" heading, respectively
 90
FIG. 5: P21011 under "S2T2" heading
 91
FIG. 5: P12019 under "S3T1" heading
 92-96
FIG. 5: P19022 ($4^{th}$) P21004, P21006, P21009 and P21011 under "S3T2" heading, respectively

DETAILED DESCRIPTION OF PREFERRED EMBODIMENTS

Figure 2A:
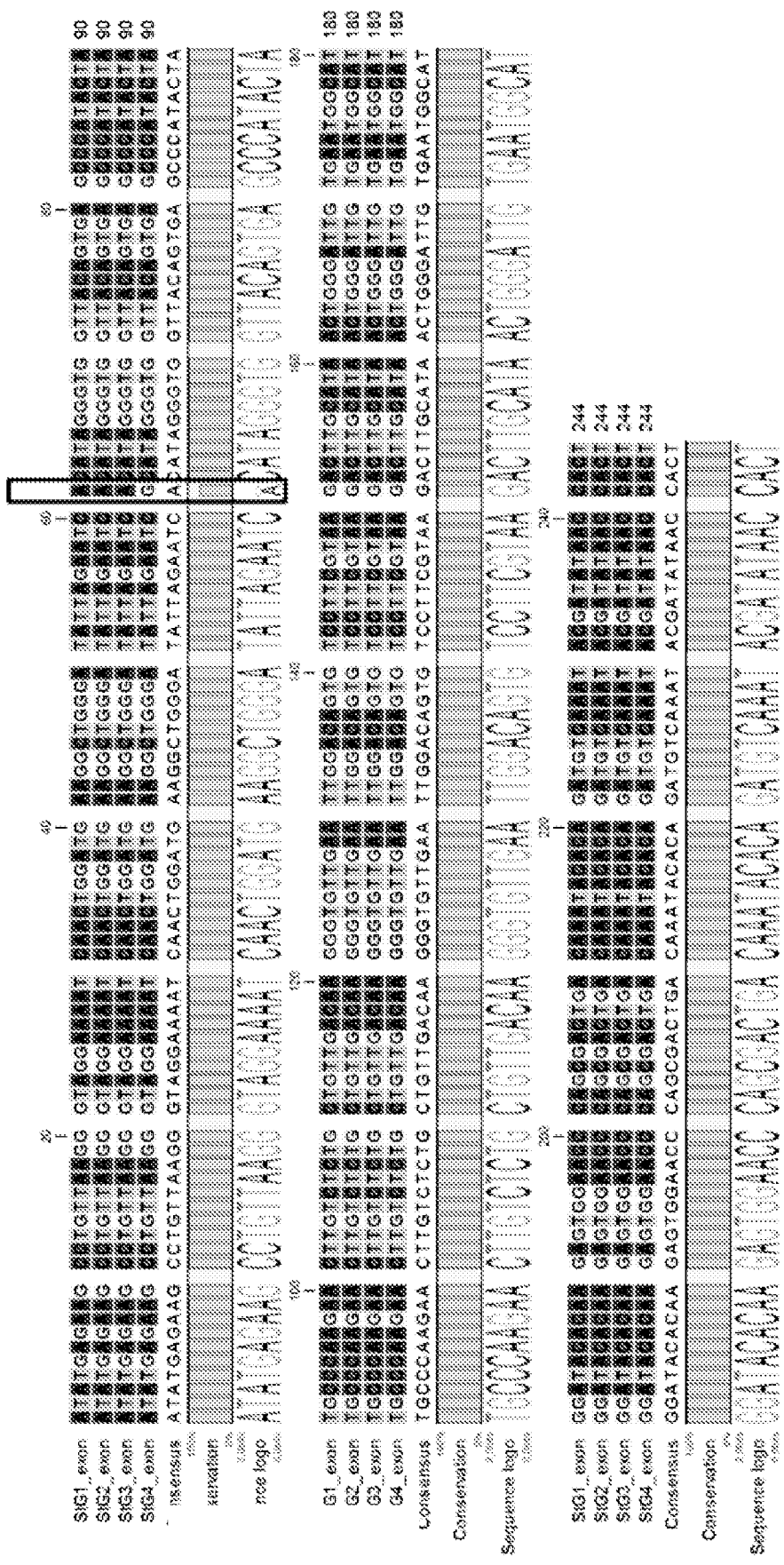
FIG. 2A: StG4_exon
 47

In one aspect the present invention relates to a method of changing the starch biosynthetic process in potato species by using a homology-directed mutagenesis for the continuous suppression of the gene function, wherein no integrated residual exogenous material is maintained in the genome of the derived potato plants. In the inventive method, the potato starch synthetic process is changed in the potato plant cell which leads to the synthesis of an amylopectin starch with no previously known properties, i.e. a novel structure, composition, and branching pattern. This is achieved by disrupting the physical gene context of genes which encode the enzymes that are involved in the synthesis of amylose and of the side chains in the amylopectin molecule. The specific disruption of the genes achieves a complete abolishment of the activities of the specific enzymes involved in the specific starch synthesis, by which starch properties and functionalities that goes beyond the state of art are obtained. With the inventive method a complete blocking of the production of one or more of the active forms of the enzymes GBSSI, SSIII, SSII is achieved, which leads to a novel starch with properties and functionalities never disclosed in literature or related patents before.

Below some definitions of some terms and expressions used throughout the application text are presented.

The term "GBSSI" is to be understood to mean any enzyme that belongs to the class of starch Granule-Bound Starch Synthases of the isoform I. Consequently the term "GBSSI gene" is to be understood to mean a nucleic acid molecule or polynucleotide (DNA, cDNA) that codes for GBSSI.

The terms "SSIII" and "SSII" are to be understood to mean a class of Soluble Starch Synthases. Soluble Starch Synthases catalyze a glycosylation reaction in which glucose moieties of the ADP-glucose substrate are transferred to an $\alpha$-1,4-linked glucan chain with formation of new $\alpha$-1,4-linkages, wherein the different classes synthesize chains of different lengths. For example, SSIIIs are described by Marshall et al. (1996, The Plant Cell 8, 1121-1135), Li et al. (2000, Plant Physiology 123, 613-624), Abel et al. (1996, The Plant Journal 10(6), 981-991) and in WO 00/66745. SSIIs are described by Edwards A. et al (Plant Journal 8, 283-294).

The terms "SSIII gene" and "SSII gene" are to be understood to mean a nucleic acid molecule or polynucleotide (DNA, cDNA) that codes for SSIII and SSII respectively. Polynucleotides coding for Soluble Starch Synthases have been described for various plant species. For potato it is disclosed by Abel et al (1996, The Plant Journal 10(6), 981-991). The term "SSIII gene" preferably means a nucleic acid molecule or polynucleotide (cDNA, DNA) that codes for SSIII in potato plants, and the term "SSII gene" preferably means a nucleic acid molecule or polynucleotide (cDNA, DNA) that codes for SSII in potato plants.

The expression "homology-directed mutagenesis" is to be understood to mean that the target sequence to be mutated in the genome is found and marked for mutagenesis by a ribonucleic acid sequence.

The term "potato" is understood to mean any potato plant belonging to the species *Solanum tuberosum.*

The expression "potato tissue" is understood to mean any part of the potato plant during any stage of its development that contains potato plant cells susceptible to the inventive method. Examples of a potato tissue are a tuber, a shoot, a leaf, a stem, and a flower.

The expression "protoplast" is understood to mean cells from any potato tissue.

The expression "CRISPR/nuclease technology" means that several variants of nucleases may be used together with CRISPR for the production of amylopectin potato starch according to the present invention. Examples of nucleases are Cas, such as Cas9, and Cpf1.

Cas9 is used in the embodiments disclosed below.

The expression "target nucleotide sequence" is understood to mean the specific nucleotide sequence located in the DNA of the potato genome to be identified with the inventive method. In the case of the use of Cas9, as nuclease, in the CRISPR/Cas complex, the target nucleotide sequence consists of 20 bp immediately upstream of a 5'-NGG-3' protospacer adjacent motif (PAM) in the cell genome.

The expression "targeting ribonucleotide sequence" is understood to mean a RNA sequence which is fully or essentially homologous to a sequence (the so called target nucleotide sequence) in the gene which is to be mutated by the method according to the invention. If type II Cas9 is used, the targeting ribonucleotide sequence preferably is 20 bp. The targeting ribonucleotide sequence is fully or essentially homologous to the target sequence, which is to be understood as being more than 75% homologous, preferably more than 85% homologous, more preferably more than 95% homologous to the target sequence. In other words, the targeting ribonucleotide sequence is able to hybridize with the complementary strand of the target sequence and in this way locate the Cas to introduce a double strand break (DSB) in the DNA strand.

The expression "essentially homologous" is to be understood to mean that said targeting ribonucleotide sequence may differ from the fully homologous one as to sequence length and base identity but only in such a way that the desired mutation still is obtained.

The expression "completely lacking amylose" used to define the "amylopectin potato starch" is understood to mean that no amylose at all has been produced in the potato plant due to the complete abolishment of the GBSSI enzyme activity.

The expression "100% amylopectin" and "0% amylose" is understood to mean the same. However, as trace amounts of amylose at least theoreti-cally can happen to be included in an amylopectin potato starch, e.g. due to contamination from the surroundings, the expressions "more than 99% amylopectin" and "more than 99.5% amylopectin" is presented with a view to covering such a situation. Nevertheless, amylopectin potato starch containing 99% or more of amylopectin is not known before. The inventive method for achieving the obstruction of the desired ones among the enzymes GBSSI, SSIII, and SSII uses a method for targeted homology-directed mutagenesis. Thus, the method according to the present invention provides targeted editing of the plant genome without leaving any residual exogenous genetic material in the resulting plant. This technology is more precisely directed to disrupting the gene context where earlier methods have been dependent on the physical insertion of a genetic device intended for the modulation of the gene expression or translation, respectively. As defined above, with homology-directed mutagenesis is meant that the target region to be mutated is found and marked for mutagenesis in the cell nucleus by a targeting ribonucleotide sequence which identifies the complementary strand of the target nucleotide sequence. In the inventive method the obstruction of the starch synthesis enzymes in question is made by the action of a sequence-specific RNA/-nuclease protein complex which is translocated to the nucleus and which acts to precisely cut the DNA at a predetermined locus of a chromosome in a potato plant cell. Error-prone repair of the cut permits the introduction of mutations and a loss of function of the gene, and thus a mutation is achieved without introducing any exogenous genetic material. In this way the disclosed technology can be used to modify plant cell material without having any residual exogenous material integrated or left in the cell. In one embodiment of the method according to the present invention for achieving said introduction of a homology-directed mutation in a plant cell, genetic material, by a sequence-specific RNA/nuclease protein complex is obtained by using the technology CRISPR/Cas9 (clustered regularly interspaced short palindromic repeats/CRISPR associated protein 9). (Doubna and Charpentier, 2014; Mahfouz et al 2014). The most widely used CRISPR/Cas originates from *Streptococcus pyogenes* [3], where it plays a role as a part of the adaptive immune system of this bacterium taking care of invading viruses or other nucleic acids. In nature, CRISPR consists of an array of sequence repeats separated by protospacers from the target genome. The resulting rather long transcript is then processed into short non-coding RNAs which can form a complex with a type II Cas9 protein. The complex binds to the corresponding region which is complementary to the protospacer region in the invading nucleic acid and makes a double strand digestion in the target region, thus inactivating the invading RNA or DNA The adapted method for directed gene mutations uses a short single guide RNA (sgRNA), containing a 20 bp guide sequence, i.e. the targeting ribonucleotide sequence used in the inventive method, a promoter and an sgRNA scaffold, which in combination with a Cas9 [3] can induce mutations in more or less any target of choice. The target sequence in the gene is 20 bp for the type II Cas9 and must be located immediately upstream a 5'-NGG-3' protospacer adjacent motif (PAM) in the cell genome. The genes which are targeted according to the present invention contain several PAMs, located both in introns and in exons. Thus, several different targeting ribonucleotide sequences may be anticipated by the disclosed invention.

Furthermore, the present invention is not limited to the targeting ribonucleotide sequence being 20 bp. In some cases the targeting ribonucleotide sequence may be shorter or longer than 20 bp, depending on i.a. the specific target sequence. Also, if another type of Cas is used, the targeting ribonucleotide sequence may be shorter or longer than 20 bp. The resulting double strand break (DSB) is repaired by the cells own repair mechanism, either through non-homologous end joining (NHEJ) or homologous recombination (HR). The repair mechanisms are error prone and often lead to inserts or deletions (indels), which may cause a gene knockout by introducing a stop codon into the gene, leading to the production of a truncated non-functional enzyme. The indels are random in size, even though small indels seem to be most common. The repair mechanisms may also lead to a frame shift, which may lead to the production of a truncated enzyme or a defect enzyme having a decreased or abolished enzyme activity. The repair mechanism may also lead to a changed number of codons, which may lead to a defect enzyme having a decreased or abolished enzyme activity. According to the present invention, no active or functional enzyme is produced in the resulting potato. This can be verified by measuring the enzyme activity by methods well known in the art, such as enzyme kinetics, histochemical studies or different biochemical studies (e.g. Zymogram, ELISA and PAGE). The presence of a mutation can be verified by conventional techniques such as PCR. Also, the absence of a functional enzyme may be verified by analyzing the composition of the produced starch, e.g. by the staining method described in Example 6 below.

If desired, base shifts or insertions can be tailor made by introduction of a repair template [4, 5], increasing the applications from only generating gene knockouts to also involve gene enhancement. The *Streptococcus pyogenes* Cas9 coding sequence can be used as such or may be codon adapted for plants or codon adapted to other organism classes or species [6][7].

The choice of promoter driving the sgRNA has been shown to impact the efficiency of generating mutations. In a study on soybean by Sun et al. 2014, a U6 promoter from soybean (*Glycine max* L.) was compared with the more generally used [8] U6 promoter from *Arabidopsis thaliana* and an increase in mutation efficiency was found when using the endogenous promoter [9]. However, it has also been shown that the strength of the promoter can have an effect on off-targets, and high concentrations of SgRNA-Cas9 transcripts can increase off-target mutations [10, 11], i.e undesired mutations.

The method according to the present invention, in which the CRISPR/Cas, preferably CRISPR/Cas 9, is used in one embodiment including a specific targeting ribonucleotide sequence as the guide sequence, will lead to 100% elimination, or inhibition, of the targeted enzyme activity in question. Thus, in the specific species, the consequence will be that the targeted biosynthetic process is totally blocked. This means that if the GBSSI gene is obstructed in the potato by the used technology there will not be any amylose synthesized in the potato and as a consequence the starch composition will be constituted by at least 99% amylopectin, preferably 100%, in view of the definition above. As suggested above, the difference between a 100% amylopectin starch and starch containing e.g. 2% or 1% amylose is substantial in view of such properties as stability and improved freeze and thaw stability. Furthermore, the impact of eliminating also the soluble starch synthase activities SSIII and or SSII will also lead to a so far unknown amylopectin starch with unique properties. The consequence of reducing the SSIII and/or SSII enzyme activities is known to lead to shorter chains of the amylopectin molecule.

Some target regions and the corresponding target nucleotide sequences of particular relevance in connection with the present invention are the following, which also are disclosed in more detail in Example 2.

```
GT1:
                                     SEQ. ID. NO. 1
    5'-GATATTAGAATCACATAGGG-3'

GT2:
                                     SEQ. ID. NO. 2
    5'-TGTTGACAAGGGTGTTGAAT-3'

GT3:
                                     SEQ. ID. NO. 3
    5'-GCTACCATTGTTTGTGGAAA-3'

GT4:
                                     SEQ. ID. NO. 4
    5'-GACAAGAAGATCCCTTTGAT-3'

S2T1:
                                     SEQ. ID. NO. 5
    5'-GTGCTAAAAGGGGTAAGTTG-3'

S2T2:
                                     SEQ. ID. NO. 6
    5'-GGGGTGCCCTTTCATCGGCC-3'

S2T3:
                                     SEQ. ID. NO. 7
    5'-GCTCCAGTAGAGAGCAAATG-3'

S3T1:
                                     SEQ. ID. NO. 8
    5'-GAACATCTGAACCAAATTTC-3'

S3T2:
                                     SEQ. ID. NO. 9
    5'-GAGGTGGCAATGGACCCAGG-3'

S3T3:
                                     SEQ. ID. NO. 10
    5'-GGAAACTAATGCCAGTAGCA-3'
```

In one embodiment of the present invention the production of the GBSSI enzyme is abolished, or inhibited, which leads to a potato which produces more than 99%, preferably 100%, amylopectin starch.

In another embodiment of the invention the enzyme activity of GBSSI and SSIII are eliminated, which leads to a potato that produces, more than 99%, preferably 100%, amylopectin starch, wherein the structure of such an amylopectin molecule is not known before. In a preferred embodiment of the invention the enzyme activity of all of GBSSI, SSIII, and SSII is eliminated, which leads to a potato which produces more than 99%, preferably 100%, amylopectin starch and in which the amylopectin structure in several aspects is totally different from the potato amylopectin structure that can be found in conventional cropped potatoes. More precisely, the structure of such an amylopectin chain can be defined as a short-chained, highly branched amylopectin, and these characteristics are known from other crops than potato to give improved stability and robustness against retrogradation.

In order to fully abolish the production of an active enzyme in a potato, the corresponding gene must be mutated in all alleles in such a way that no protein with enzyme activity is produced, that a truncated enzyme having no enzyme activity is produced or that a mutated enzyme having no enzyme activity is produced. Importantly, according to the present invention, the mutation may or may not be the same in all alleles. Thus, different parts of the gene may be mutated in different alleles. The same part of the gene may also be mutated in different ways in different alleles. Potato genotypes having 2 or more alleles, most commonly 4 alleles, are known.

Thus, with the method according to the present invention four different varieties of potato may be produced, wherein also four different starch qualities may be synthesized, namely "gbssI-potato starch", "gbssI/ssIII-potato starch", "gbssI/ssII-potato starch" and "gbssI/ssII/ssIII-potato starch", all with individual characteristics as to the composition of amylose and amylopectin ratio and as to the amylopectin structure. As a consequence thereof, its function in food and non-food applications is correlated to the solution stability from the altered starch composition.

Thus, in one aspect the present invention refers to an amylopectin potato starch which in one embodiment contains at least 99% amylopectin, preferably 100% amylopectin, and which in another embodiment additionally is provided with shorter chains and a higher degree of branching in the amylopectin molecule compared to native potato amylopectin.

More precisely, the fact that the amylopectin chains in the amylopectin potato starch according to the present invention in average are shorter than the chains of potato amylopectin means that the amylopectin chains in the amylopectin potato starch according to the present invention in average automatically also have a higher degree of branching than the chains in native potato amylopectin. More precisely, the degree of branching is more than 5%, preferably more than 6%.

The amylopectin potato starch according to the present invention may in its most preferred embodiments (two or three enzymes eliminated) be defined and differentiated compared to conventional amylopectin potato starches by a freeze/thaw stability test (in which less than 30% syneresis is obtained after 2-4, preferably 2, repeated freeze/thaw cycles, alternatively less than 15% syneresis after 4 repeated freeze/thaw cycles. This test is presented in a poster at the V International Oat Conference & VII International Barley Genetics Symposium Jul. 30-Aug. 6, 1996 at the University of Saskatchewan, Saskatoon, Canada, by Å. Ståhl, G. Persson, L-Å Johansson, and H. Johansson with the poster "Breeding barley for functional foodstarch".

As disclosed above, the starch biosynthetic process in a potato plant is changed in the inventive method by targeted mutagenesis using the CRISPR/Cas method, preferably the CRISPR/Cas9 method, which introduces mutations in the gene loci encoding the GBSSI, SSIII and SSII enzymes. The achieved mutation/mutations lead(s) to a complete disruption of the activity of the GBSSI, SSIII, and SSII enzymes in the potato plant cell, which leads to a new potato genotype which synthesizes a starch consisting of, more than 99%, preferably 100%, amylopectin type molecules with unique properties compared to the parental potato it is derived from.

For the production of the CRISPR/Cas9 complexes the transcription unit for sgRNA and encoding Cas9 can reside on the same or separate physical DNAs. The gene constructs are not limited to the sgRNA and the Cas9 disclosed above. In the case of other variants of Cas, the target nucleotide sequence may be shorter or longer than 20 bp.

In one embodiment of the inventive method, gene constructs encoding sgRNA and Cas9 nuclease are transfected to potato protoplasts. The DNA encoding sgRNA and Cas9 is transiently expressed in the cell and is not transferred to later generations, thus not leaving any residual exogenous DNA in the resulting potato.

In a second embodiment, sgRNA and Cas9 protein are produced outside the potato cell and are introduced by e.g. microinjection. According to this embodiment, no exogenous DNA is introduced into the cell, and thus there will be no residual exogenous DNA in the resulting potato.

In a third embodiment, T-DNAs encoding sgRNA and Cas9 are stably introduced by particle bombardment or Agrobacterium mediated transformation, using Agrobacterium tumefaciens. Agrobacterium introduction of T-DNA can be performed by well-known transformation methods in the art, e.g. leaf disc or stem transformation or by agroinfiltration. DNA encoding sgRNA and Cas9 nuclease can in a preferred embodiment be transiently operating in the potato cell or be stably introduced in the potato genome. Stably introduced DNA can subsequently be separated from introduced mutations by crossing, leading to a potato having no residual exogenous DNA. Importantly, the introduced mutation is stably transferred across the generations, thus giving rise to a new potato in which GBSSI and SSII and/or SSIII do not show any enzyme activity.

The cultivated potatoes are normally tetraploid and such potatoes are preferably used for the introduction of mutations. However, the methods and means disclosed here are also applicable for potato genotypes of higher or lower ploidy level, e.g. for diploid genotypes. There are several methods well known in the art to change the ploidy level of potato cells.

sgRNAs, i.e. the targeting ribonucleotide sequences, targeting one or several locations in the same gene as well as sgRNAs targeting several different genes and optionally different locations of these genes can be applied in one and the same introduction of mutational constructs or assemblies. Thus, one or more locations in the same gene can be targeted in the same step and/one or more genes can be targeted in the same step.

Different methods can be used for the identification of successfully mutated genes. Identifications of mutations can preferably be performed by PCR and fragment analysis for identification of indels via high resolution capillary electrophoresis.

Several methods for the identification of mutations in specific loci are known in the art such as PCR coupled to melting point analysis of an applied probe, PCR and sequencing of amplified fragments spanning the targeted region for mutation or detection using CAPS, a method based on the loss of function of a restriction site located in the predicted cleavage site in the target region.

The methods disclosed can be applied in multiple rounds of application to introduce mutations in all alleles of a gene or to introduce mutations in more than one gene or to introduce additional mutations in additional genes where application of targeting several genes has occurred. More specifically, already mutated genotypes can be stably transformed or agroinfiltrated, or used for production of protoplasts and transfected or microinjected for introduction of additional mutations.

In one embodiment of the invention at least one allele of one gene is mutated in one application of the CRISPR/Cas9 complex. In a more preferred embodiment mutations are introduced into several alleles of one or several genes in one application of the CRISPR/Cas9 complex. In an even more preferred embodiment of the invention all alleles of a gene or several genes are mutated in one application of mutation method. Importantly, to reach mutations in all alleles of a gene, additionally rounds of application of the CRISPR/Cas9 complex might be needed.

Starch from the potato, in which the enzyme activities of GBSSI and/or SSIII, and/or SSII have been eliminated according to the above description, is extracted and purified by washing the potato with water at room temperature in a rotating washing drum. The potatoes are grinded/rasped with cell disintegrators to liberate the starch granules from the cells. The potato mash obtained containing granular starch, fibers, and proteins is further screened using mesh sizes in the area from 60-160 µm of the screen so that the fiber material is separated from the starch granules and the solubilized protein fraction. The starch suspension is further processed using screening equipment in which the potato fruit juice, consisting of solubilized potato protein and other nutritional components, is separated from the starch. The starch is mixed with fresh water and washed clean using hydrocyclone equipment, decanter or washing centrifuge in which the water is changed and the starch is thereby washed until the protein level in the refined starch is less than 0.2% measured by the Kjeldahl nitrogen content method, with a conversion factor of 6.25. The starch slurry is dewatered on a rotating vacuum filter to a dry matter (DM) of 55-65%. The starch suspension is dried in a flash drier to approx. 78-82% w/w DM. The purified starch is collected and stored at room temperature. The disclosed invention is not limited to the described extraction and purification method although it is considered to be basic knowledge and for a skilled man in the art how starch from potato tubers are produced.

Before drying, the starch can be separated into different granular sizes giving one fraction with small granules of less than 25 µm, one fraction with large granules, i.e. 25-60 µm, or very large granules of more than 60 µm. Alternatively, it can be fractionated dry into different granular sizes. The present invention is not limited to the extraction processing of the starch from the potato, as this is considered to be common knowledge in starch manufacturing.

The purified inventive starch may be inhibited by alkaline roasting or bleaching reaction with oxidizing agents. It may also be pre-gelatinized and further dried with spray drying or drum drying to a dry content of more than 80% w/w DM, preferably more than 85% w/w DM, even more preferably more than 90% w/w DM. It may also be degraded to a molecular weight of 100 000-1 000 000 Da, preferably 300 000-800 000 Da, even more preferably 500 000-700 000 Da, with enzymatic modification or acid treating or pyrodextrinization or oxidation degradation, or combinations thereof.

Consequently, the achieved starch based on the obstruction of the production of the GBSSI and/or SSIII and/or SSII enzymes is freeze/thaw stable and has an extremely enhanced stability, i.e. robustness against retrogradation, after being partly or totally gelatinized in a liquid suspension and preferably, but not exclusively, in the use for food applications.

In another aspect of the present invention the inventive amylopectin potato starch may be used in several different applications. In one embodiment, the purified novel amylopectin potato starch may be used in food applications in its native state. The starch may alternatively be used in a modified state, wherein the starch has been modified by anyone of the modification methods known by a skilled man in the art. The most common modification methods are cross-linking, phosphorylation, acetylation, hydroxypropylation, 2-octenylsuccinylation with both the sodium and the aluminium salt forms, succinylation, cationization, oxidation, enzymatic modification, acid treatment of starch, pyrodextrinization and alkaline roasting of starches as well as combinations thereof. The present invention is not limited to the modification methods disclosed, as chemical or non-chemical modifications are considered as basic know-how. Thus, all kinds of modifications described in literature and publications can be applied on the inventive amylopectin potato starch products.

The applications in which the purified inventive amylopectin potato starch can be used are common food applications in which starch and modified starches normally are used and can be found in literature. The common applications are, but not limited to: fruit preparations, soups and sauces, confectionary, dairy products like yoghurt, créme fraiche, processed cheese, as a stabilizer of oil in water (O/W) emulsions as well as water in oil (W/O) emulsions in liquid products and spreads and/or emulsions which are spray dried into a powder, e.g. spray dried functional oils like DHA, ARA, vitamin E etc. Further to this, the product can be used in coating applications like batters and breading's for deep fried potatoes, vegetables, chicken, beef etc.

To conclude, the purified amylopectin starch may be used in the following food applications:
- as a texturizer in liquid formulations, wherein the starch concentration is 0.05-15% w/w, preferably 0.5-10% w/w, more preferably 1.5-6% w/w,
- as a texturizer in formulations wherein the food product is additionally frozen,
- preferably in coating applications in which a vegetable or animal derived food product is coated with the starch and/or starch in a formulation with other ingredients, and followed by additional deep frying.
- as a stabilizer of water-in-oil (W/O) emulsions in liquid products and spreads, or
- as an emulsion stabilizer for oil-in-water (O/W) emulsions in a liquid state and in applications where the oil-in-water emulsion is additionally spray dried to a powder, wherein said amylopectin potato starch first has been modified with sodium octenyl succinate or aluminium octenyl succinate.

Further, the purified amylopectin starch may also be used in paper applications, preferably for surface sizing and coating of paper, or as a wet-end starch in paper production.

In a further aspect, the present invention also encompasses a product containing said amylopectin potato starch, wherein the nature of said product is related to any one of the above mentioned uses.

EXPERIMENTS

Example 1—Sequencing of Target Genes

Information about the GBSSI, SSII, and SSIII genes are shown in FIG. 1, wherein A represents the *Solanum tubero-* sum GBSSI gene (GenBank accession No. A23741.1), in which 13 exons are marked with arrows. Sequencing primers covering 508 bp of exon 8 and splice regions are marked with StGBSSExf and StGBSSExr. Target regions are marked with GT1, GT2, GT3, and GT4. FIG. 1B represents the *Solanum tuberosum* SSII gene (GenBank accession No. NW_006238930.1), in which 8 exons are marked with arrows. Sequencing primers covering 1352 bp of exon 1 and splice regions are marked StSSExon f and StSS2Exon r. Target regions are marked with S2T1, S2T2 and S2T3. FIG. 1C represents the *Solanum tuberosum* SSIII gene (GenBank accession No. NW_006239023.1), in which 15 exons are marked with arrows. Sequencing primers covering 966 bp of exon 3 and splice regions are marked StSS3Exf and StSS3Exr. Target regions are marked with S3T1, S3T2 and S3T3.

Allelic variation of parts of the GBSS, SSII, and SSIII genes in the tetraploid potato variety Kuras was determined as described below. The results of a determination of single exons of the target genes are shown in FIG. 2 A-C.

The GBSS Gene

Genomic DNA from the potato variety Kuras was used to amplify a 508 bp fragment of the GBSS gene, covering exon 8 as well as adjacent introns (StGBSSExf and StGbSSExr, see FIG. 1A). Genomic DNA from leaf tissue of Kuras was extracted using a Gene Jet Plant Genomic DNA Purification Mini Kit (Thermo Fisher Scientific, Waltham USA). 250 ng DNA was used as template in a PCR reaction with 0.5 μmol of primers StGBSSExf and StGBSSExr (Sigma-Aldrich, Saint Louis, USA), Phusion HF polymerase, dNTP, and HF buffer (Thermo Fisher Scientific, Waltman, USA) according to the suppliers instructions.

The primers used were,

```
StGBSSExf:
                              SEQ. ID. NO. 11
5'-CCTCTTCTCAATCTTCCTGATGAATTCAG-3'

StGBSSExr:
                              SEQ. ID. NO. 12
5'-AGAGCCTCCTTTAGTAAAGGTTTTGCGTC-3'
```

The amplification was performed with the following cycling conditions:

| 1. | 98° 1 min |
| 2. | 98° 10 s |
| 3. | 64° 10 s |
| 4. | 72° 15 s |
| 5. | Step 2-4 30 cycles |
| 6. | 72° for 10 minutes |

The PCR products were ligated to pJET1.2/blunt using a CloneJET PCR Cloning Kit (Thermo Fisher Scientific, Waltham, USA) following transformation to One Shot® TOP10 Chemically Competent *E. coli* (Invitrogen, Carlsbad, USA). After 1 night incubation at 37° C. on LB plates containing 100 μg/mL ampicillin, randomly picked colonies were subjected to DNA isolation and sequenced by Sanger sequencing (GATC Biotech, Konstanz, Germany).

The sequenced alleles of exon 8 (marked StG1-StG4) in the GBSS gene were compared to each other and the results showed that all alleles were highly homologous (See FIG. 2), and that only one allele had a sequence variation in exon 8 with an adenine (A)→guanine (G) shift at one positon (marked with a box in FIG. 2 A showing 244 bp of the 508 bp fragment). The results also showed that the 3 identical alleles (StG1-StG3) had a 100% homology to a published GBSS gene (GenBank accession No. A23741.1).

The SSII Gene

Genomic DNA from the potato variety Kuras was used to amplify a 1352 bp fragment of the SSII gene, covering exon 1 as well as adjacent introns (StSS2Exon f and StSS2Exon r). Genomic DNA from leaf tissue of Kuras was extracted using Gene Jet Plant Genomic DNA Purification Mini Kit (Thermo Fisher Scientific, Waltham USA). 250 ng DNA is used as template in a PCR reaction with 0.5 μmol of primers (Sigma-Aldrich, Saint Louis, USA), Phusion HF polymerase, dNTP, and HF buffer (Thermo Fisher Scientific, Waltman, USA) according to the suppliers instructions.

The primes used were;

```
StSS2Exon f:
                              SEQ. ID. NO. 13
5'-TGCTTCACAATCCCTAATTCTC-3'

StSS2Exon r:
                              SEQ. ID. NO. 14
5'-ATCCAAAAGTGTCTCTTGACTG-3'
```

Amplification was performed with the following cycling conditions;

| 1. | 98° 1 min |
| 2. | 98° 20 s |
| 3. | 63° 30 s |
| 4. | 72° 30 s |
| 5. | Step 2-4 30 cycles |
| 6. | 72° for 10 minutes |

Figure 2B:
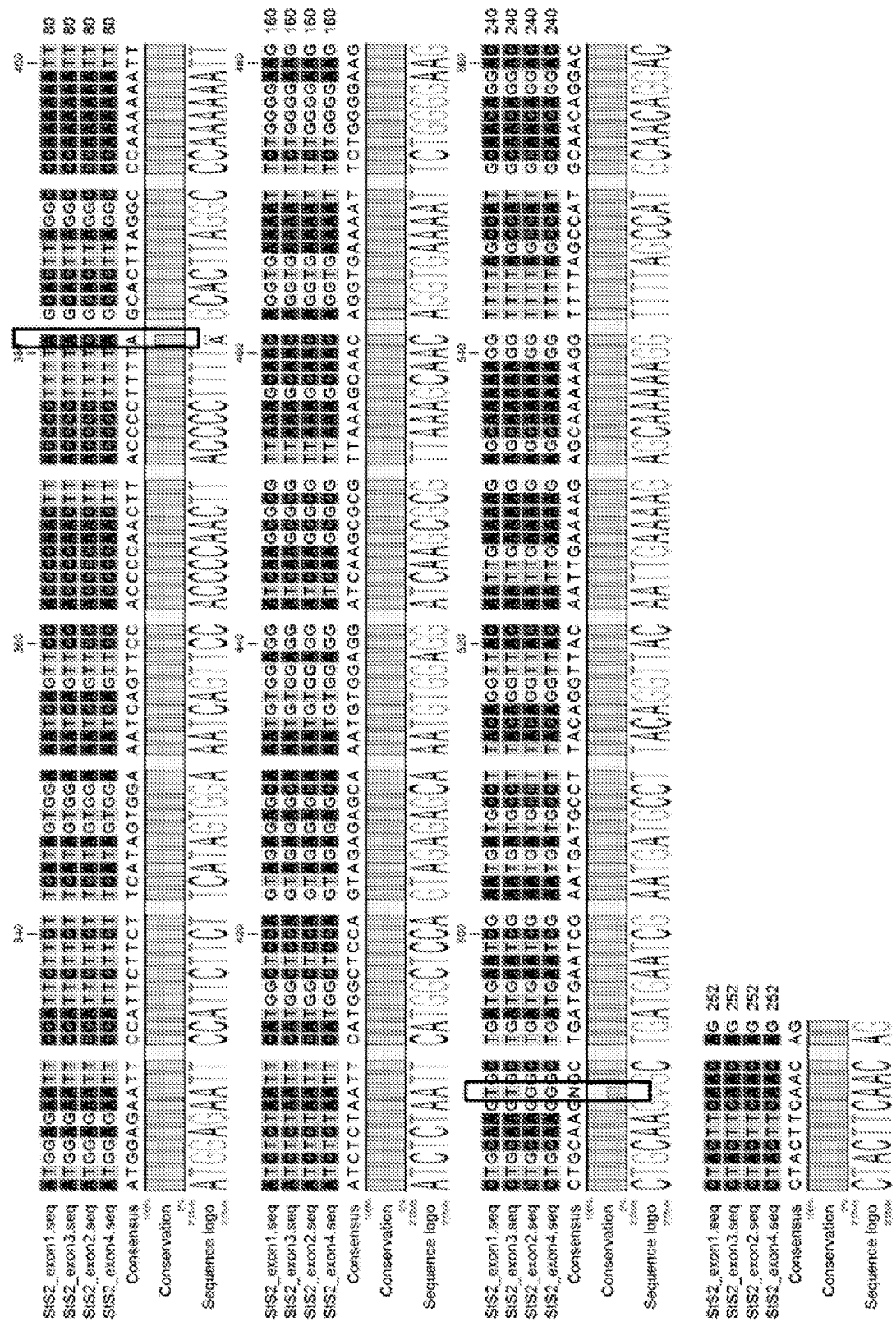
FIG. 2B: StS2_exon1 and StS2_exon3 (all equivalent sequences)
 48

The PCR product was ligated to pJET1.2/blunt using a CloneJET PCR Cloning Kit (Thermo Fisher Scientific, Waltham, USA) following transformation to One Shot® TOP10 Chemically Competent *E. coli* (Invitrogen, Carlsbad, USA). After 1 night incubation at 37° C. on LB plates containing 100 μg/mL ampicillin, randomly picked colonies were subjected to DNA isolation and sequenced (GATC Biotech, Konstanz, Germany). The sequenced alleles of exon 1 (marked StS2_exon1-StS2_exon4) in the SSII gene were compared to each other. Base shift variations were found at two positions (FIG. 2B), one position with an adenine (A)→cytosine (C) shift and one position had a guanine (G)→thymine (T) shift (marked with boxes in FIG. 2B showing 252 bp of the 1352 bp fragment).

The SSIII Gene

Genomic DNA from leaf tissue of Kuras was extracted using a Gene Jet Plant Genomic DNA Purification Mini Kit (Thermo Fisher Scientific, Waltham USA). 250 ng DNA was used to isolate a 966 bp gene fragment covering exon 3 as well as adjacent introns of SSII (StSS3Exf and StSS3Exr, see FIG. 1 C). A PCR reaction was performed with 0.5 μmol of primers StSSExf and StSSExr (Sigma Aldrich, Saint Louis, USA), Phusion HF polymerase, dNTP, and HF buffer (Thermo Fisher Scientific, Waltman, USA) according to the supplier's instructions.

The primers used were;

```
StSS3Exf:
                              SEQ. ID. NO. 15
5'-GCTTAGAGAAGCGGCTATGCGTG-3'

StSS3Exr:
                              SEQ. ID. NO. 16
5'-TCCATCATATATGCATCCAATGGAACC-3'
```

Amplification was performed with the following cycling conditions;

| | | |
|---|---|---|
| 1. | 98° 1 min | |
| 2. | 98° 10 s | |
| 3. | 64° 10 s | |
| 4. | 72° 15 s | |
| 5. | Step 2-4 30 cycles | |
| 6. | 72° for 10 minutes | |

The PCR product was ligated to pJET1.2/blunt using a CloneJET PCR Cloning Kit (Thermo Fisher Scientific, Waltham, USA) following transformation to One Shot® TOP10 Chemically Competent *E. coli* (Invitrogen, Carlsbad, USA). After 1 night incubation at 37° C. on LB plates containing 100 μg/mL ampicillin, randomly picked colonies were subjected to DNA isolation and sequenced (GATC Biotech, Konstanz, Germany).

Figure 2C:
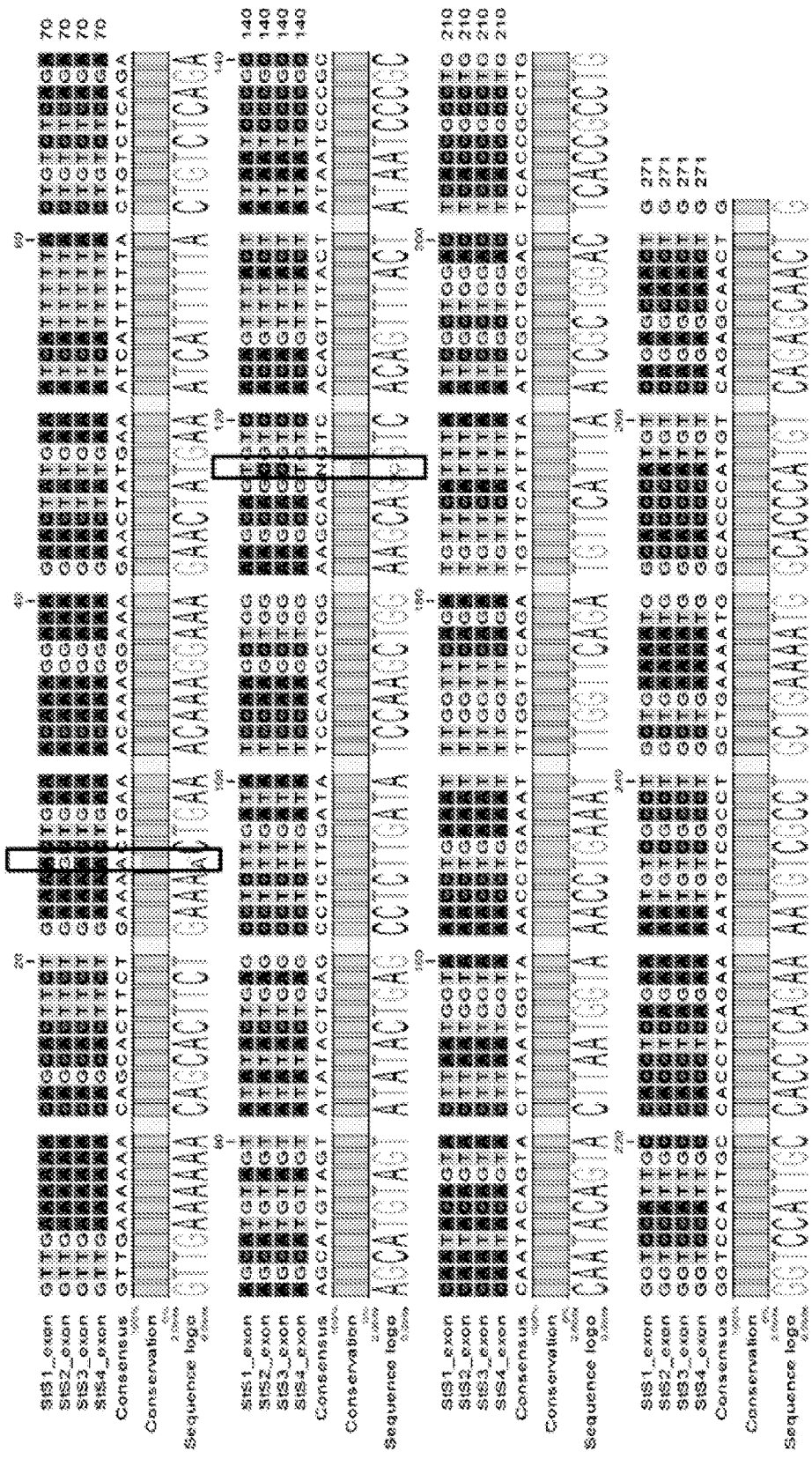
FIG. 2C: StS1_exon and StS4_exon (all equivalent sequences)
 52

The sequenced SSIII alleles of exon 3 (marked StS1-StS4) were compared to each other. Two of the four sequenced SSIII alleles were found having base shift variations (FIG. 2C) in exon 3 with an adenine (A)→guanine (G) shift in one allele and cytosine (C)→thymine (T) in two of the alleles (marked with boxes in FIG. 2C showing 271 bp of the 966 bp fragment).

Example 2—Constructs Targeting the GBSSI, SSII, and SSIII Genes

The different target regions in the GBSSI, SSII, and SSIII genes are shown in FIG. 1.

Figure 3:
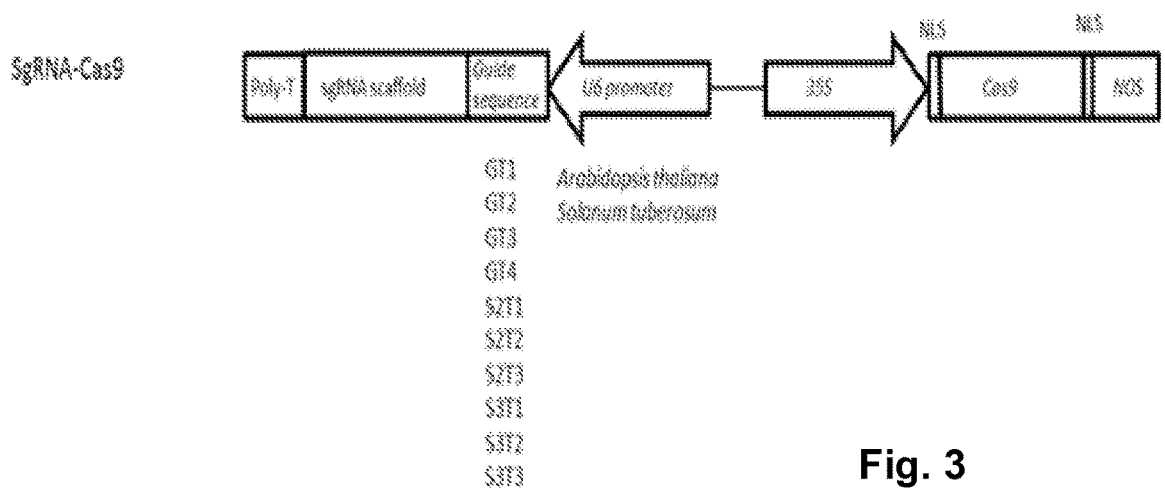
FIG. 3 shows constructs designed for CRISPR/Cas9 mediated induction of mutations in the GBSSI, SSII, and SSIII gene.

FIG. 3 is a schematic drawing of a construct designed for CRISPR/Cas9 mediated induction of mutations in the GBSS, SSII, and SSIII genes. From left to right; terminator (poly-T), sgRNA scaffold, target regions (either of GT1, GT2, GT3, GT4, S2T1, S2T2, S2T3, S3T1, S3T2, or S3T3), U6 promoter of either *Arabidopsis thaliana* or *Solanum tuberosum* origin, 35S promotor of cauliflower mosaic virus origin (CaMV), nuclear localization sequence (NLS), plant codon optimized Cas9(Cas9) gene, NLS and terminator (NOS).

Constructs Targeting the GBSSI Gene

Four target regions for inducing mutations in the GBSS gene were selected and named GT1, GT2, GT3 and GT4 (see FIG. 1A), each target region consisting of 20 bp located directly upstream a 5'-NGG-3' PAM site and with, except for GT2, the nucleotide G in the 5' end. The target regions were identified and selected using a CRISPR-design web based tool (http://crispr.mit.edu/). GT1 and GT2 are located within exon 8, with GT1 spanning a region with an allelic variation, while GT3 is located in exon 1 and GT4 is located in exon 9 (GenBank accession no. A23741.1). The four target sequences are all located on the positive strand in the GBSS gene.

Target sequences,

GT1:
                                          SEQ. ID. NO. 1
5'-GATATTAGAATCACATAGGG-3'

GT2:
                                          SEQ. ID. NO. 2
5'-TGTTGACAAGGGTGTTGAAT-3'

GT3:
                                          SEQ. ID. NO. 3
5'-GCTACCATTGTTTGTGGAAA-3'

GT4:
                                          SEQ. ID. NO. 4
5'-GACAAGAAGATCCCTTTGAT-3'

A fragment containing a promoter, a guide sequence, i.e. the targeting ribonucleotide sequence homologous to the target sequence, and a sgRNA scaffold were synthetically produced for each of the four guide RNAs and were received cloned in a pEx-A2 vector (Eurofins Genomics, Ebersberg, Germany). A U6 promoter of *Arabidopsis thaliana* (GenBank accession no. X52527.1 or *Solanum tuberosum* origin (GenBank accession No. Z17290.1) was chosen for driving the expression of the guide sequence and the sgRNA scaffold (see FIG. 3). The fragments had an additional XhoI site synthesized at the 5" end of the fragment. Since the U6 promoter is dependent on a G nucleotide at the 5' end of the guide sequence to initiate transcription, a G was synthetically added at position 1 of the GT2 targeting nucleotide sequence. The synthesized fragments were cloned together with a Cas9 gene driven by a 35S promoter in the standard Gateway® entry vector pENTR11 (Invitrogen, Carlsbad, USA) using 3-fragment cloning (see FIG. 3). All constructs were transformed to One Shot® TOP10 Chemically Competent *E. coli* (Invitrogen, Carlsbad, USA). Additionally, Cas 9 and target guide GT1 expression cassettes in their original vectors were transformed to One Shot® TOP10 Chemically Competent *E. coli* (Invitrogen, Carlsbad, USA) for co-expression.

Constructs Targeting the SSII Gene

Three target regions for SSII were selected and named S2T1, S2T2 and S2T3 (See FIG. 1 B), both located directly upstream a 5'-NGG-3' PAM site and with the nucleotide G in the 5' end of a 20 bp fragment adjacent the PAM site. The target regions were identified using the CRISPR-design web based tool (http://crispr.mit.edu/). S2T1 is located on the negative strand and S2T3 on the positive strand within exon 1, and S2T2 is located on the negative strand in exon 2 (GenBank accession no. NW_006238930.1.

Target sequences,

S2T1:
                                          SEQ. ID. NO. 5
5'-GTGCTAAAAGGGGTAAGTTG-3'

S2T2:
                                          SEQ. ID. NO. 6
5'-GGGGTGCCCTTTCATCGGCC-3'

S2T3:
                                          SEQ. ID. NO. 7
5'-GCTCCAGTAGAGAGCAAATG-3'

A fragment containing a promoter, a guide sequence, i.e. the targeting ribonucleotide sequence homologous to the target sequence, and a sgRNA scaffold were synthetically produced for the three guide RNAs (Eurofins Genomics, Ebersberg, Germany). A U6 promotor of *Arabidopsis thaliana* (X52527.1) origin was used for driving the expression of the guide sequence and the sgRNA (see FIG. 3). The fragments had an additional XhoI site synthesized at the 5' end. The synthesized fragments were cloned together with a Cas9 gene driven by a 35S promoter in the standard Gateway® entry vector pENTR11 (Invitrogen, Carlsbad, USA) using 3-fragment cloning (FIG. 3). All constructs were transformed to One Shot® TOP10 Chemically Competent *E. coli* (Invitrogen, Carlsbad, USA).

Constructs Targeting the SSIII Gene

Three target regions for SSIII were selected and named S3T1, S3T2 and S3T3 (see FIG. 1C), each located directly upstream a 5'-NGG-3' PAM site and with the nucleotide G in the 5' end of a 20 bp fragment adjacent the PAM site. The target regions were identified using the CRISPR-design web based tool (http://crispr.mit.edu/). S3T1 is located on the negative strand and S3T2 is located on the positive strand within exon 4 and S3T3 is located on the positive strand in exon 1 (GenBank accession no. NW_006239023.1).

Target sequences:

```
S3T1:
                                       SEQ. ID. NO. 8
5'-GAACATCTGAACCAAATTTC-3'

S3T2:
                                       SEQ. ID. NO. 9
5'-GAGGTGGCAATGGACCCAGG-3'

S3T3:
                                       SEQ. ID. NO. 10
5'-GGAAACTAATGCCAGTAGCA-3'
```

A fragment containing a promoter, a guide sequence, i.e. the targeting ribonucleotide sequence homologous to the target sequence, and a sgRNA scaffold were synthetically produced for each of the guide RNAs (Eurofins Genomics, Ebersberg, Germany). A U6 promotor of *Arabidopsis thaliana* (X525origin was used for driving the expression of the guide sequence and the sgRNA (see FIG. 3). The fragments had an additional XhoI site synthesized at the 5'. The synthesized fragments were cloned together with a Cas9 gene driven by a 35S promoter in the standard Gateway® entry vector pENTR11 (Invitrogen, Carlsbad, USA) using 3-fragment cloning (see FIG. 3). All constructs were transformed to One Shot® TOP10 Chemically Competent *E. coli* (Invitrogen, Carlsbad, USA).

Example 3—qRNA Synthesis and Design of RNA-Protein Complex (RNP)

One target region each for inducing mutations in GBSS (GT4), SSII (S2T3) and SSIII (S3T2) were selected to produce gRNA using GeneArt™ Precision gRNA Synthesis Kit (Thermo Fisher Scientific, Waltham, USA) according to the supplier's instructions.

Primers;

```
GT4 + T7f
                                       SEQ.ID.NO. 39
TAATACGACTCACTATAGACAAGAAGATCCCTTTGAT

GT4 + trRNAr
                                       SEQ.ID.NO. 40
TTCTAGCTCTAAAACATCAAAGGGATCTTCTTGT

S3T2 + T7f
                                       SEQ.ID.NO. 41
TAATACGACTCACTATAGAGGTGGCAATGGACCCAGG

S3T2 + trRNAr
                                       SEQ.ID.NO. 42
TTCTAGCTCTAAAACCCTGGGTCCATTGCCACCT

S2T3 + T7f
                                       SEQ.ID.NO. 43
TAATACGACTCACTATAGCTCCAGTAGAGAGCAAATG

S2T3 + trRNAr
                                       SEQ.ID.NO. 44
TTCTAGCTCTAAAACCATTTGCTCTCTACTGGAG
```

The respective gRNAs were composed of a U6 promoter, a guide sequence and a RNA scaffold/tracer RNA. Respective gRNA was incubated with GeneArt™ Platinum™ Cas9 Nuclease (Thermo Fisher Scientific, Waltham, USA) for 10 minutes at room temperature before transfected to purified protoplast.

Example 4—PEG Mediated Protoplast Transfection and Regeneration

Table 1 below shows results of a protoplast transfection experimental setup. The experiments are numbered P1000-P21000. Targeting nucleotide sequences, PEG (%), DNA (µg), transfection time (min), and the number of protoplasts used was varied and defined for each experiment. The mutation frequency (%) is calculated for each experiment based on mutated lines detected, using high resolution fragment analysis, of the total number of regenerated lines analyzed. The frequency of lines with more than 1 allele mutated (%) is calculated based on multiple mutated alleles detected, using high resolution fragment analysis and Sanger sequencing, of all mutated lines found in experiment.

The potato cultivar Kuras was propagated in 1× Murashige and Skoog (MS) medium including vitamins (pH 5.8) including 3% sucrose, 8 µM silver thiosulphate (STS), and 0.7% phytoagar (Duchefa, Haarlem, The Netherlands) in a controlled environmental chamber at 24° C. for 16 h in light and 20° C. for 8 h in dark.

Homology-directed induction of mutations was made in, 1) GBSSI, 2) GBSSI+SSIII, 3) GBSSI+SSII, and 4) GBSSI+SSII+SSIII, by transfection of one, two or three of the above described constructs or RNPs in protoplasts isolated from top leaf tissue of five to six weeks old potato plantlets. Transient expression was preferred over traditional transformation to avoid stable integration of DNA in the genome. However, stable transformation following crossings and segregation of inserted genetic material is also used with the aim to induce targeted mutations in said genes. Transfection quality DNA, isolated from above described constructs, were purified with a Qiagen Plasmid Mini Kit (Qiagen, Hilden, Germany) according to manufacturer's instructions.

Transient expression of the sgRNA-Cas9 constructs with the targeting ribonucleotide sequences homologous to the target regions GT1, GT2, GT3, GT4, S2T1, S2T2, S2T3, S3T1, S3T2, and S3T3 as well as expression of the targeting ribonucleotide-complex and Cas9 from separate vectors, were made through a PEG-mediated transfection method. Furthermore, RNP of GT4, GT4+S3T2, and GT4+S3T2+S2T2 was delivered to protoplasts using the same PEG-mediated transfection method. The protoplast isolation and transfection method was based on a method described by Nicolia et al 2014 [12], adapted for the CRISPR/Cas9 method. The transfection was performed at room temperature using $1.0 \times 10^5$ or $1.6 \times 10^5$ protoplasts in 100 µl, 12.5, 25 or 40% PEG4000 (Sigma-Aldrich, Saint Louis, USA) and 5, 10 or 15 µg of purified DNA during an incubation time of 3 or 30 min (Table 1). After transfection, the protoplasts were embedded in alginate (Sigma-Aldrich, Saint Louis, USA) and were incubated at 25° C. in dark until the first cell division took place. During the following 2 weeks the light was stepwise increased and reached full light (Memmert, Schwarbach, Germany) when callus visible to naked eye was formed. Approximately four weeks after transfection, each callus was released and incubated in liquid media for additionally two to four weeks for further callus development and shoot induction. The enlarged calli were then transferred to solid medium for shoot development.

Regeneration, i.e development of shoots from the enlarged calli, was found in all of the different experimental setups used (see Table 1 in Example 5 below). The first shoot emerged approximately 3 months after transfection and up to 25% of all calli had developed a shoot after 6 months.

Example 5—Mutational Screening Using High Resolution Fragment Analysis

Screening for induced mutations of a large number of pooled calluses or regenerated plants was made using a high resolution fragment analysis based on 96-format DNA extraction, PCR amplification and capillary electrophoresis. Individual lines were numbered consecutively based on the experiment, e.g P1001, P1002 etc (see also FIG. 5). Callus or a leaf sample of approximately 5×5 mm in diameter from a 2-4 weeks old plantlet of each regenerated shoot was homogenized in 500 µl lysis buffer (100 mM Tris, 50 mM EDTA and 1% SDS, pH 9.0) in a Retsch Mixer Mill MM400 for 30 s at 30 Hz (Retsch, Haan, Germany). DNA was extracted from 200 µl cleared lysate in a Qiacube HT extraction robot using a QIAamp 96 DNA QIAcube HT Kit utilising the standard DNA extraction protocol provided by the supplier (Qiagen, Hilden, Germany) with addition of RNAse A to a final concentration of 0.1 mg/ml in the elution buffer. PCR amplification was made on 0.5 µl isolated DNA using Phusion HF polymerase (Invitrogen, Carlsbad, USA) according to the manufacturer's instructions. The forward primers were labelled at the 5' end with the fluorescent dyes FAM, NED or PET (Thermo Fisher Scientific, Waltham USA) depending on the target gene.

Primers:

```
GT1 and GT2
StGBSSexon1f:
                            SEQ. ID. NO. 17
FAM-5'-ACTGGATGAAGGCTGGGATA-3'

StGBSSexon1f:
                            SEQ. ID. NO. 17
VIC-5'-ACTGGATGAAGGCTGGGATA-3'

StGBSSexon1r:
                            SEQ. ID. NO. 18
5'-ATTTGTCAGTCGCTGGGTTC-3'

GT3
StGBSS(GT3)f:
                            SEQ. ID. NO. 19
FAM-5'-AGGAACCATACTCTGACTCAC-3'

StGBSS(GT3)f:
                            SEQ. ID. NO. 19
VIC-5'-AGGAACCATACTCTGACTCAC-3'

StGBSS(GT3)f:
                            SEQ. ID. NO. 20
5'-TTTTGCTCCAAGGACCAAC-3'

GT4
StGBSS(GT4)f:
                            SEQ. ID. NO. 21
FAM-5'-TCTCTATACAGGTCATGGACG-3'

StGBSS(GT4)f:
                            SEQ. ID. NO. 21
VIC-5'-TCTCTATACAGGTCATGGACG-3'

StGBSS(GT4)f:
                            SEQ. ID. NO. 22
5'-GCAGCAACAAGAATATCTGAAC-3'

S2T1
StSS2(S2T1)f:
                            SEQ. ID. NO. 23
PET-5'-TGGAAATCAGTTCCACCCC-3'

StSS2(S2T1)f:
                            SEQ. ID. NO. 23
VIC-5'-TGGAAATCAGTTCCACCCC-3'

StSS2(S2T1)r:
                            SEQ. ID. NO. 24
5'-CATGGCTAAAACCTTTTTGCTC-3'

S2T2
StSS2(S2T1)f:
                            SEQ. ID. NO. 25
PET-5'-CGATAAAAATACACCGCCTGC-3'

StSS2(S2T1)f:
                            SEQ. ID. NO. 25
VIC-5'-CGATAAAAATACACCGCCTGC-3'

StSS2(S2T1)r:
                            SEQ. ID. NO. 26
5'-TCTGGAGGGACATTCAACG-3'

S3T1 and S3T2
StSS3(S3T1, S3T2)f:
                            SEQ. ID. NO. 27
NED-5'-ATCCAAGCTGGAAGCAGTGT-3'

StSS3(S3T1, S3T2)f:
                            SEQ. ID. NO. 27
VIC-5'-ATCCAAGCTGGAAGCAGTGT-3'

StSS3(S3T1, S3T2)r:
                            SEQ. ID. NO. 28
5'-GACATGGGTGCCATTTTCAG-3'

S3T3
StSS3(S3T3)f:
                            SEQ. ID. NO. 29
NED-5'-TGATGACAAGGATGCTGTAAAG-3'

StSS3(S3T3)f:
                            SEQ. ID. NO. 29
VIC-5'-TGATGACAAGGATGCTGTAAAG-3'

StSS3(S3T3)r:
                            SEQ. ID. NO. 30
-5'-TCAACATCCACCTGCAATATC-3'
```

The amplification was performed with the following cycling conditions;

| 1. | 98° 1 min |
|---|---|
| 2. | 98° 10 s |
| 3. | 64° 10 s |
| 4. | 72° 15 s |
| 5. | Step 2-4 30 cycles |
| 6. | 72° for 10 minutes |

0.5 µl of the PCR product (diluted 1:20) was mixed with 0.5 µl wild type control PCR fragment (diluted 1:20) and 9.0 µl Hi-Di™ Formamide (Thermo Fisher Scientific, Waltham USA), incubated at 95° for 3 minutes and chilled on ice. The wild type control fragment, amplified under the same PCR conditions but using a diverging labelled primer (VIC-labelled), was added to each sample in order to distinguish alleles with indels from non-mutated alleles (see FIG. 4). High resolution fragment separation was performed on a 3500 Genetic analyser (Thermo Fisher Scientific, Waltham USA) according to the manufacturer's instructions. Data was handled with a 3500 Series Data Collection Software 3. Mutated alleles were identified by the presence of more than one peak in the obtained raw data (see FIG. 4).

Figure 4:
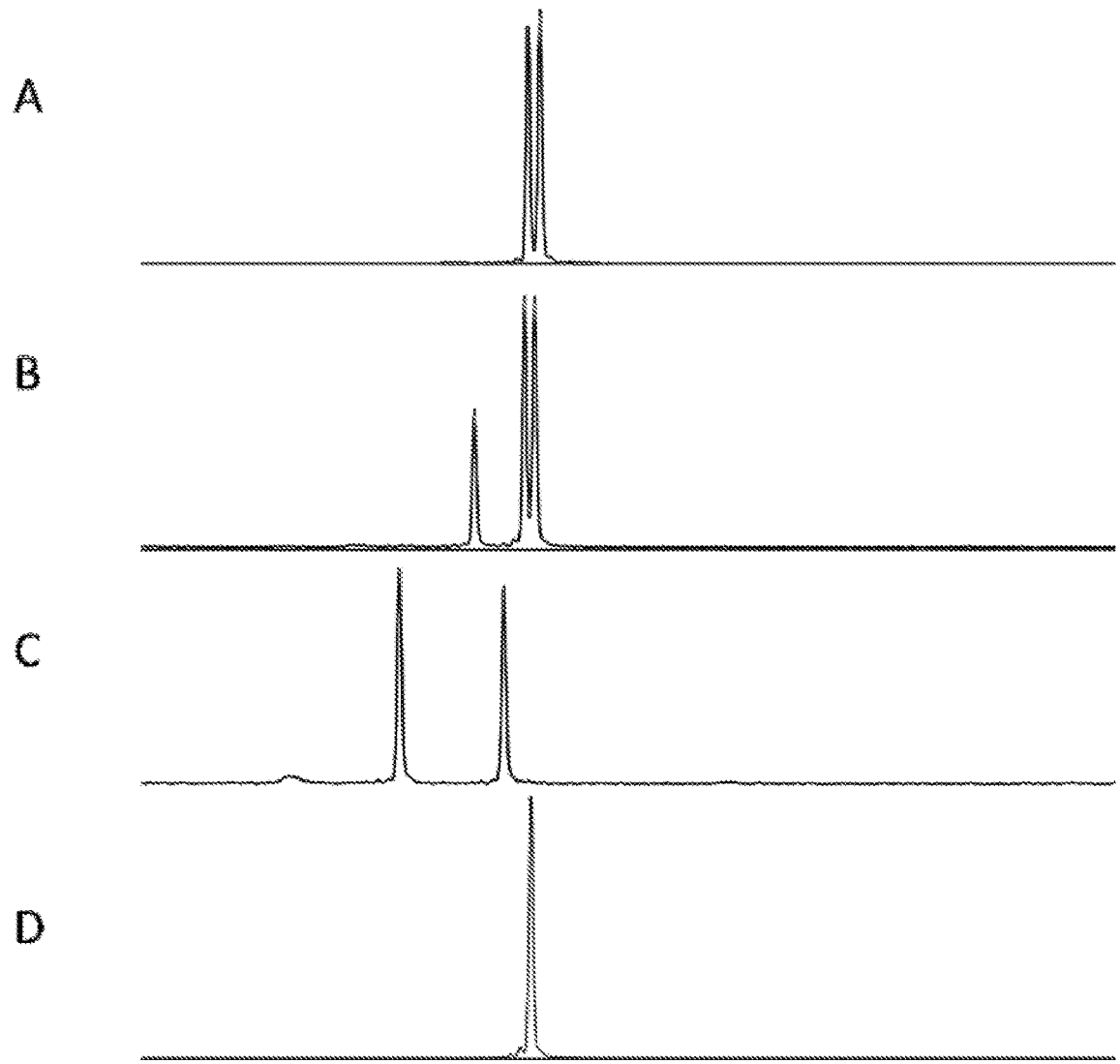
FIG. 4 shows diagrams of the result of high resolution fragment analysis of CRISPR/Cas9 mediated induction of mutations of the GBSSI gene, more precisely A) line with at least one allele mutated having a one bp deletion, B) line with at least two alleles mutated having one and six bp deletions, C) a line with all four alleles mutated having 2 and 8 bp deletions and D) parental line

FIG. 4 shows the results of a high resolution fragment analysis of CRISPR/Cas9 mediated mutations of the GBSSI gene, exemplified by lines mutated in the GT1 target region. A represents Line P1003 with 1 mutated allele detected, B represents Line P1004 with 2 mutated alleles detected, C represents Line P10084 with 4 mutated alleles detected verified by lack of wild type allele and D represents the wild type GBSS gene fragment.

The results show that mutations were induced using all transfection conditions used. The results also show that mutations are induced using any of the target regions described (see Table 1 below). Inserts and deletions (indels) down to 1 bp were detected with the described method. Multiple alleles with induced indels differing in size were distinguished by visible multiple peaks (see FIG. 4).

TABLE 1

| Experiment | Target sequence | Promoter | PEG (%) | DNA (ug) | Transfection time (min) | Number of protoplasts | Lines analyzed | Mutated lines | Mutation frequency (%) | Lines with >1 allele mutated | Frequency of lines >1 allele mutated |
|---|---|---|---|---|---|---|---|---|---|---|---|
| P1000 | GT1 | At | 25 | 5 | 3 | 160000 | 85 | 7 | 8.2 | 3 | 42.9 |
| P2000 | GT1 | At | 25 | 5 + 5 | 3 | 160000 | 130 | 3 | 2.3 | 1 | 33.3 |
| P3000 | GT2 | At | 25 | 5 | 3 | 160000 | 214 | 2 | 0.9 | 0 | 0.0 |
| P5000 | GT1 | At | 12.5 | 10 | 3 | 160000 | 149 | 7 | 4.7 | 2 | 28.6 |
| P6000 | GT1 | At | 40 | 15 | 30 | 100000 | 17 | 4 | 23.5 | 1 | 25.0 |
| P7000 | GT2 | At | 12.5 | 10 | 3 | 160000 | 208 | 11 | 5.3 | 1 | 11.1 |
| P8000 | GT2 | At | 40 | 15 | 30 | 100000 | 36 | 2 | 5.6 | 1 | 50.0 |
| P9000 | GT3 | St | 40 | 15 | 30 | 100000 | 71 | 1 | 1.4 | 1 | 100 |
| P10000 | GT4 | St | 12.5 | 10 | 3 | 160000 | 157 | 9 | 5.7 | 3 | 37.5 |
| P11000 | GT4 | St | 40 | 15 | 30 | 100000 | 118 | 2 | 1.7 | 1 | 50.0 |
| P12000 | GT1 | At | 25 | 5 + 5 | 3 | 100000 | 30 | 5 | 16.7 | 3 | 60.0 |
| P12000 | S3T1 | At | 25 | 5 + 5 | 3 | 100000 | 30 | 1 | 3.33 | 1 | 100 |
| P13000 | GT2 | At | 25 | 5 + 5 | 3 | 100000 | 38 | 4 | 10.5 | 1 | 25.0 |
| P13000 | S3T1 | At | 25 | 5 + 5 | 3 | 100000 | 38 | 0 | 0 | 0 | 0 |
| P14000 | GT1 + GT2 | At | 25 | 5 + 5 + 5 | 3 | 100000 | 57 | 8 | 14.0 | 4 | 50.0 |
| P14000 | S3T1 | At | 25 | 5 + 5 + 5 | 3 | 100000 | 57 | 1 | 1.8 | 1 | 100 |
| P15000 | GT1 + GT2 | At | 25 | 5 + 5 | 3 | 100000 | 41 | 4 | 9.8 | 0 | 0 |
| P17000 | GT3 | At | 40 | 6.5 + 15 | 30 | 100000 | 10 | 1 | 10.0 | 0 | 0 |
| P17000 | S3T3 | At | 40 | 6.5 + 15 | 30 | 100000 | 10 | 2 | 20.0 | 0 | 0 |
| P18000 | GT4 | At | 40 | 15 + 15 | 30 | 100000 | 20 | 6 | 30.0 | 1 | 16.7 |
| P18000 | S3T2 | At | 40 | 15 + 15 | 30 | 100000 | 20 | 4 | 20.0 | 0 | 0 |
| P19000 | GT3 | At | 40 | 6.5 + 15 + 15 | 30 | 100000 | 19 | 2 | 10.5 | 0 | 0 |
| P19000 | S2T1 | At | 40 | 6.5 + 15 + 15 | 30 | 100000 | 19 | 7 | 36.8 | 5 | 71.4 |
| P19000 | S3T2 | At | 40 | 6.5 + 15 + 15 | 30 | 100000 | 19 | 3 | 15.8 | 1 | 33.3 |
| P20000 | GT4 | At | 40 | 15 + 1.8 + 15 + 15 | 30 | 100000 | 21 | 3 | 14.3 | 0 | 0 |
| P20000 | GT3 | At | 40 | 15 + 1.8 + 15 + 15 | 30 | 100000 | 21 | 0 | 0 | 0 | 0 |
| P20000 | S2T2 | At | 40 | 15 + 1.8 + 15 + 15 | 30 | 100000 | 21 | 1 | 4.8 | 0 | 0 |
| P20000 | S3T3 | At | 40 | 15 + 1.8 + 15 + 15 | 30 | 100000 | 21 | 1 | 4.8 | 0 | 0 |
| P21000 | GT4 | At | 40 | 15 + 15 + 15 | 30 | 100000 | 16 | 1 | 6.25 | 0 | 0 |
| P21000 | S2T2 | At | 40 | 15 + 15 + 15 | 30 | 100000 | 16 | 1 | 6.25 | 0 | 0 |
| P21000 | S3T2 | At | 40 | 15 + 15 + 15 | 30 | 100000 | 16 | 5 | 31.3 | 4 | 80.0 |

Table 2 shows the results of a high resolution fragment analysis of RNP CRISPR/Cas9 mediated mutations of the GBSSI gene, SSII gene, and SSIII gene on a pool of calluses.

TABLE 2

| RPN | No of calli | Indels detected |
|---|---|---|
| GT4 | 4 | −4, −2, 0 |
| GT4 | 3 | −9, −6, −4, 0, 1 |
| S3T2 | 3 | −4, −2, −1 |
| GT4 | 10 | −5, −4, −2, 0 |
| S3T2 | 10 | −2, 0 |
| GT4 | 10 | −15, −6, −5, −3, −2, 0 |
| S3T2 | 10 | −6, −3, −2, 0, 1 |

Example 6—Analysis of Mutations

FIG. 5 shows the results of genotyping of individual alleles with induced mutations in GT1, GT2, GT3, GT4, StT1, S2T2, S3T1, and S3T3 target regions. P1000-P21000 are individual lines. Deleted nucleotides are shown with hyphens, and inserted nucleotides are shown in bold. The PAM site is underlined in each wild type (WT) fragment.

Lines of mutations identified with the high resolution fragment analysis method were subjected to genotyping to determine the exact size and location of the mutation. PCR amplification covering the respective target region in the individual lines were cloned and analyzed by DNA sequencing (Eurofins Genomics, Ebersberg, Germany). Fragments spanning the predicted Cas9-cut site was amplified using 0.5 µl isolated DNA (described under Example 4), 0.25 µM of each forward and reverse primer and with Phusion polymerase (Invitrogen, Carlsbad, USA) according to the manufacturer's instructions.

Primers:

```
GT1 and GT2
StGBSSexon1f:
                                  SEQ. ID. NO. 17
5'-ACTGGATGAAGGCTGGGATA-3'

StGBSSexon1r:
                                  SEQ. ID. NO. 18
5'-ATTTGTCAGTCGCTGGGTTC-3'

GT3
StGBSS(GT3)f:
                                  SEQ. ID. NO. 19
5'-AGGAACCATACTCTGACTCAC-3'

StGBSS(GT3)f:
                                  SEQ. ID. NO. 20
5'-TTTTGCTCCAAGGACCAAC-3'

GT4
StGBSS(GT4)f:
                                  SEQ. ID. NO. 21
5'-TCTCTATACAGGTCATGGACG-3'

StGBSS(GT4)f:
                                  SEQ. ID. NO. 22
5'-GCAGCAACAAGAATATCTGAAC-3'

S2T1
StSS2(S2T1)f:
                                  SEQ. ID. NO. 23
5'-TGGAAATCAGTTCCACCCC-3'

StSS2(S2T1)r:
                                  SEQ. ID. NO. 24
5'-CATGGCTAAAACCTTTTTGCTC-3'

S2T2
StSS2(S2T1)f:
                                  SEQ. ID. NO. 25
5'-CGATAAAAATACACCGCCTGC-3'

StSS2(S2T1)r:
                                  SEQ. ID. NO. 26
5'-TCTGGAGGGACATTCAACG-3'

S3T1 and S3T2
StSS3(S3T1, S3T2)f:
                                  SEQ. ID. NO. 27
5'-ATCCAAGCTGGAAGCAGTGT-3'

StSS3(S3T1, S3T2)r:
                                  SEQ. ID. NO. 28
5'-GACATGGGTGCCATTTTCAG-3'

S3T3
StSS3(S3T3)f:
                                  SEQ. ID. NO. 29
5'-TGATGACAAGGATGCTGTAAAG-3'

StSS3(S3T3)r:
                                  SEQ. ID. NO. 30
-5'-TCAACATCCACCTGCAATATC-3'
```

The amplification was performed with the following cycling conditions;

| 1. | 98° 1 min |
| 2. | 98° 10 s |
| 3. | 64° 10 s |
| 4. | 72° 15 s |
| 5. | Step 2-4 30 cycles |
| 6. | 72° for 10 minutes |

The PCR products were ligated to pJET1.2/blunt using a CloneJET PCR Cloning Kit (Thermo Fisher Scientific, Waltham, USA) following transformation to One Shot® TOP10 Chemically Competent E. coli (Invitrogen, Carlsbad, USA). After 1 night incubation at 37° C. on LB plates containing 100 µg/mL ampicillin, randomly picked colonies were sequenced (GATC Biotech, Konstanz, Germany).

The results confirm that mutations are induced in the GBSSI, SSII and SSIII genes. The results also show that mutations are induced in multiple genes when constructs targeting two or three genes are co-transfected (Table 1, FIG. 5). The results also confirmed that mutations were induced using any experimental conditions used. Furthermore, mutations are induced in one or multiple alleles, independent of the experimental conditions and the targeting nucleotide sequence used, with the exception of GT1 flanking an allelic variation (Table 1). The mutation frequencies were found to be up to 37%, depending on the experimental setup. The frequency of multiple alleles mutated was found to be generally very high, and in a few experimental setups as high as 100% of detected mutated lines (see Table 1). To gain a complete disruption of enzyme activities, all 4 alleles of the used tetraploid potato genotype were targeted for each gene. To reach mutations in all 4 alleles of a gene, additionally rounds of protoplast isolation and transfection are applied when needed.

Example 7—In-Vitro Microtuber Production

Shoots are grown on a microtuber induction medium consisting of 4.4 g/L MS-medium, 2.5 mg/L kinetin, 0.5 mg/L abscisic acid (ABA), 8% sucrose, and 200 mg/L claforan in dark at 25° C. After 2-5 weeks microtubers have developed and are harvested. Microtubers are crushed and stained with Lugol's solution (6.7 g/L KI+3.3 g/L I2) mixed with glycerol (1:1). The starch composition is visualized under light microscope where microtubers having >92% amylopectin content are stained red-brown in color while starch containing >9% amylose is stained blue. Starch is extracted by grinding microtubers in 2 ml 70% EtOH, followed by filtration through a nylon filter with a small mesh size. 8 ml 70% ethanol is added to the samples, followed by centrifugation at 1000×g for 10 min. The ethanol is removed and the starch is left to air-dry in room temperature overnight. The isolated starch is further used for analysis as described under Examples 8-10.

Example 8—Greenhouse Minituber Production

Mutated lines are grown in soil in a greenhouse at 16 hours, 18/15° C. day/night temperature, supplementary light intensity of approximately 200 µmol s$^{-1}$m$^2$ photons and 60% relative humidity. Each line is planted as in-vivo cuttings in biological replicates in 7.5 L pots. Starch is isolated from developed minitubers by homogenization in a fruit juicer. Tris-HCl (pH 7.5, 50 mM), Na-dithionite (30 mM), and EDTA (10 mM) is added to the liquid fraction. Starch granules are allowed to sediment. The granules are washed four times with the same buffer and three times with acetone before drying overnight at room temperature. The isolated starch is further used for analysis as described under Examples 9-11.

Example 9—Starch Stability Evaluation

A 3% w/w water suspension of starch is prepared by mixing 15 g DM of the purified gbssI-PS (potato starch), gbssI/ssIII-PS and gbssI/ssII-PS, and gbssI/ssIII/ssII-PS starch, respectively, with 500 g water. The starch suspensions are heated in a water bath to 95° C. and kept at 95° C. for 30 minutes during continuous agitation. The starch solutions are put in a refrigerator for cooling down to 20° C. and consequently kept at room temperature. The viscosity of the solution is measured at room temperature with a Brookfield LV directly after the solution has reached 20° C. and methodically once per day for 7 days. As reference, similar procedures were performed with commercialized available amylopectin starches, i.e. waxy maize starch with less than 1% amylose (WMS), commercialized waxy potato starch with less than 2% amylose (WPS), commercialized available waxy rice starch with less than 4% amylose (WRS) and commercially available waxy barley starch with less than 0.5% amylose (WBS).

The experiment demonstrates that the solutions of the starches obtained with the method according to the present invention are more stable than commercially available waxy potato starch. It is also clear that the starch solution based on the gbssI/ssIII/ssII-PS is significantly more stable and thus robust against retrogradation compared with both the available waxy potato starch but also compared with the commercialized available waxy maize starch. The result further proves that starches obtained with the method according to the present invention are not known before and that the robustness against retrogradation from the potato starches can be defined as WPS <(gbssI-PS)<(gbssI/ssII-PS)<(gbssI/ssIII-PS)<(gbssI/ssIII/ssII-PS).

Example 10—Starch Retrogradation Evaluation

A 5% (w/w) water suspension of starch is prepared by mixing 22.5 g DM of the purified gbssI-PS, gbssI/ssII-PS, gbssI/ssIII-PS, and gbssI/ssIII/ssII-PSstarch, respectively, with distilled water to a total weight of 450 g. The starch suspension is put into a Brabender Amyloviscograph model E, using a 700 cmg torsion spring. In the Brabender Amyloviscograph the starch suspension is heated to 95° C. and is after the holding time of 15 min cooled to 25° C. The viscosity is continuously measured and printed during the cooling phase. The starch pastes are stored at room temperature and are further measured with a Stable Micro System Texture Analyzer for 7 days. As reference, similar procedures were performed with commercially available amylopectin starches, i.e. waxy maize starch with less than 1% amylose (WMS), commercially available waxy potato starch with less than 2% amylose (WPS), commercially available waxy rice starch with less than 4% amylose (WRS), and commercially available waxy barley starch with less than 0.5% amylose (WBS).

This experiment shows that the setback viscosity during the Brabender run is not as large as the starch paste behavior during storage and in this aspect they are totally different compared to the waxy starches. It can be concluded that no waxy starches have any tendency to give strong viscosity increases during cooling as it can be expected from starches with higher amylose contents which will lead to gel formation due to the retrogradation phenomenon correlated to the amylose content. From experiments using the texture analyzer it can be concluded that the gel formation is less for the novel presented amylopectin potato starches compared with commercially available waxy potato starch which clearly demonstrates that the stability of the starch is improved. When the starches are divided according to their gel strength after 7 days it will give the following order; WPS/gbssI-PS/gbssI/ssII-PS/WMS/gbssI/ssIII-PS/WRS/gbssI/ssIII/ssII-PS/WBS. Thus, the experiment shows that the starches obtained with the method according to the present invention are not known before and exhibit stability properties which are significantly different compared with commercially available potato starches.

Example 11—Freeze and Thaw Evaluation

The starch solutions prepared in example 10 are, after cooling to room temperature, put into 50 ml centrifuge tubes and are further centrifuged at 1500×g for 10 minutes. Thereafter, the water in the centrifuge tubes is siphoned off and weighed. The remaining concentrated starch in the tubes is frozen in a freezer at −18° C. for approximately 24 h. The starch paste is thawed and the solutions are further centrifuged at 1500×g for 10 minutes.

The procedure is repeated and the siphoned water, which is defined as syneresis, after each freeze/thaw cycle is calculated as the accumulated water loss. By dividing the amount of accumulated water loss after each freeze/thaw cycle with the starting weight of water in the solution, the per-centage of syneresis can be defined for each starch product.

The results show that waxy maize starch exhibits 30% syneresis after one freeze/thaw cycle, waxy potato starch exhibit 55% syneresis after one freeze/thaw cycle, waxy rice starch exhibits 0% syneresis after one freeze/thaw cycle but 14% after two freeze/thaw cycles, and waxy barley starch exhibits 0% after the three first freeze/thaw cycles and 7% after the fourth freeze/thaw cycle. The starches obtained with the method performs better than gbssI-PS, which performs better than WPS, but less than WRS and WMS, gbssI/ssIII-PS performs better than WRS, but less than WBS, and gbssIII/ssII-PS performs better than WRS and comparable to WBS. It is clear that the freeze/thaw stability of the starches obtained with the method according to the present invention, is significantly improved compared to the commercially available waxy potato starch. It is also clear that the solution based on the gbssI/ssIII/ssII-PS is significantly more freeze/thaw stable compared to both the available waxy potato starch and also compared to the commercially available waxy maize starch and waxy rice starch and is comparable to waxy barley starch. The result further proves that starches obtained with the method according to the present invention are novel and that the degree of freeze/thaw stability can be ranked as (gbssI-PS)<(gbssI/ssII-PS)<(gbssI/ssIII-PS)<(gbssI/ssIII/ssII-PS).

Example 12—Starch Composition in Mutated Lines

An analysis of a starch composition is performed essentially according to a modified method of Sargeant and Wycombe (1982) and Klucinec, J. D., D. B. Thompson (1998)) "*Method for determination of amylose content and amylopectin chain distribution*". The starch is dispersed in potassium hydroxide, neutralised and precipitated with ethanol. The precipitate is dispersed and dissolved in DMSO at 100° C., mixed with sodium acetate buffer, and again heated. After cooling to 45° C., isoamylase is added. The sample is incubated overnight, whereafter the enzyme is inactivated at 100° C. The solution is filtered through 0.45 μm and injected in the HPSEC system.

The High Performance Size Exclusion Chromatography (HPSEC) system consists of the following parts: A high pressure pump, an autosampler with a 500 μl loop, a RI (refractive index) detector, a column oven heated to 70° C., a magnetic stirrer and a chromatography data system. Three PL-gel 10 μm Mixed-B 300×7.5 mm polystyrene divinyl benzene analytical columns and one PL-gel 10 10 μm Mixed-B 100×7.5 mm guard column is used for the separation. The eluent is 50 mM lithium bromide in 100% DMSO, and the flow rate is 0.5 ml/min.

Since the starch is debranched the amylose fraction has the highest molecular weight and elutes fastest through the SEC columns, while the amylopectin has been degraded into single chains and elutes after the amylose.

The chromatogram is split at the retention time corresponding to DP 200 ($M_w$~34 000 g/mol) which is the transition of amylose to amylopectin in debranched potato starch.

Figure 6:
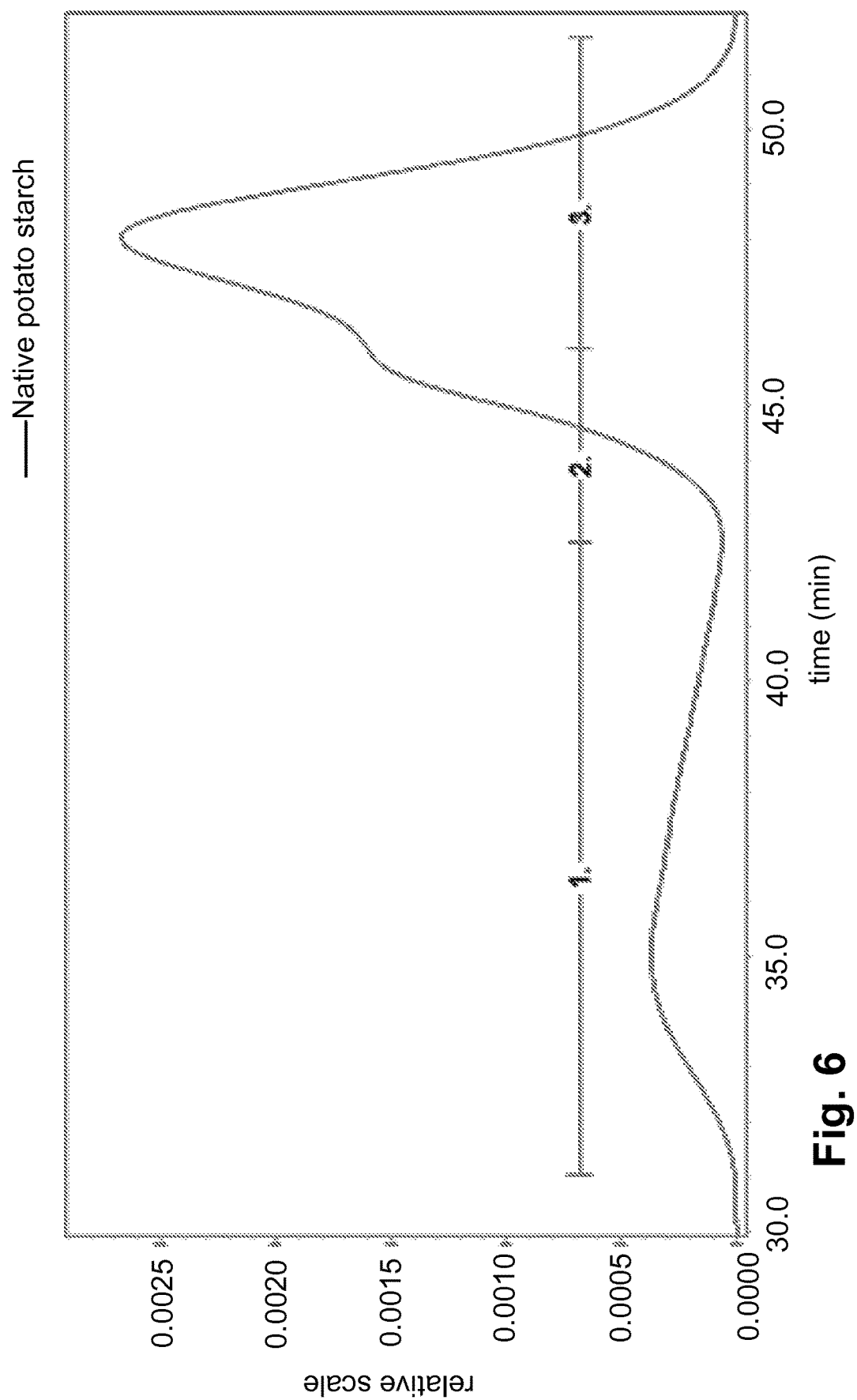
FIGS. 6-9 show results of analyses of a starch composition isolated from a number of individual mutated lines by use of a HPSEC system.

The determination of amylopectin and amylose in the starch is carried out on a High Performance Size Exclusion Chromatography system. Before the sample is injected into the separation system it is solublized in NaOH and debranched with isoamylase. After the digestion of the amylopectin the amylose fraction has the biggest molecules and is eluted first through the separation system. The retention times for amylose and amylopectin are all based on the chromatogram (FIG. 6) of debranched native potato starch (full scale produced at Lyckeby Starch AB, Sweden). The material eluted in the first peak (1. in FIG. 6) is considered amylose, and the material eluted later in the chromatogram is then amylopectin (2+3. in FIG. 6). The amylopectin fraction is split between long chained amylopectin (2. in FIG. 6) and short chained amylopectin (3. in FIG. 6).

Figure 7:
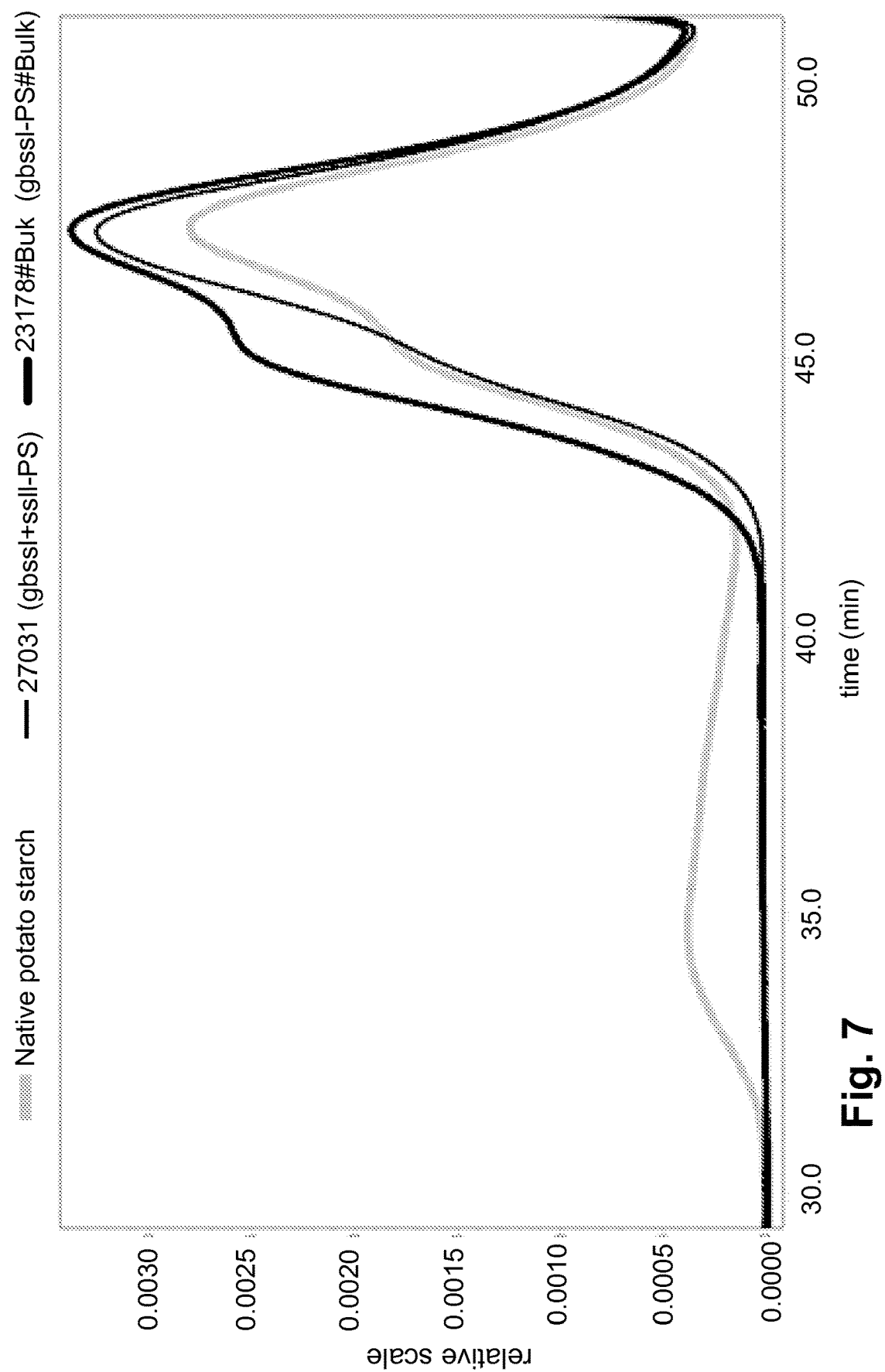
Figure 8:
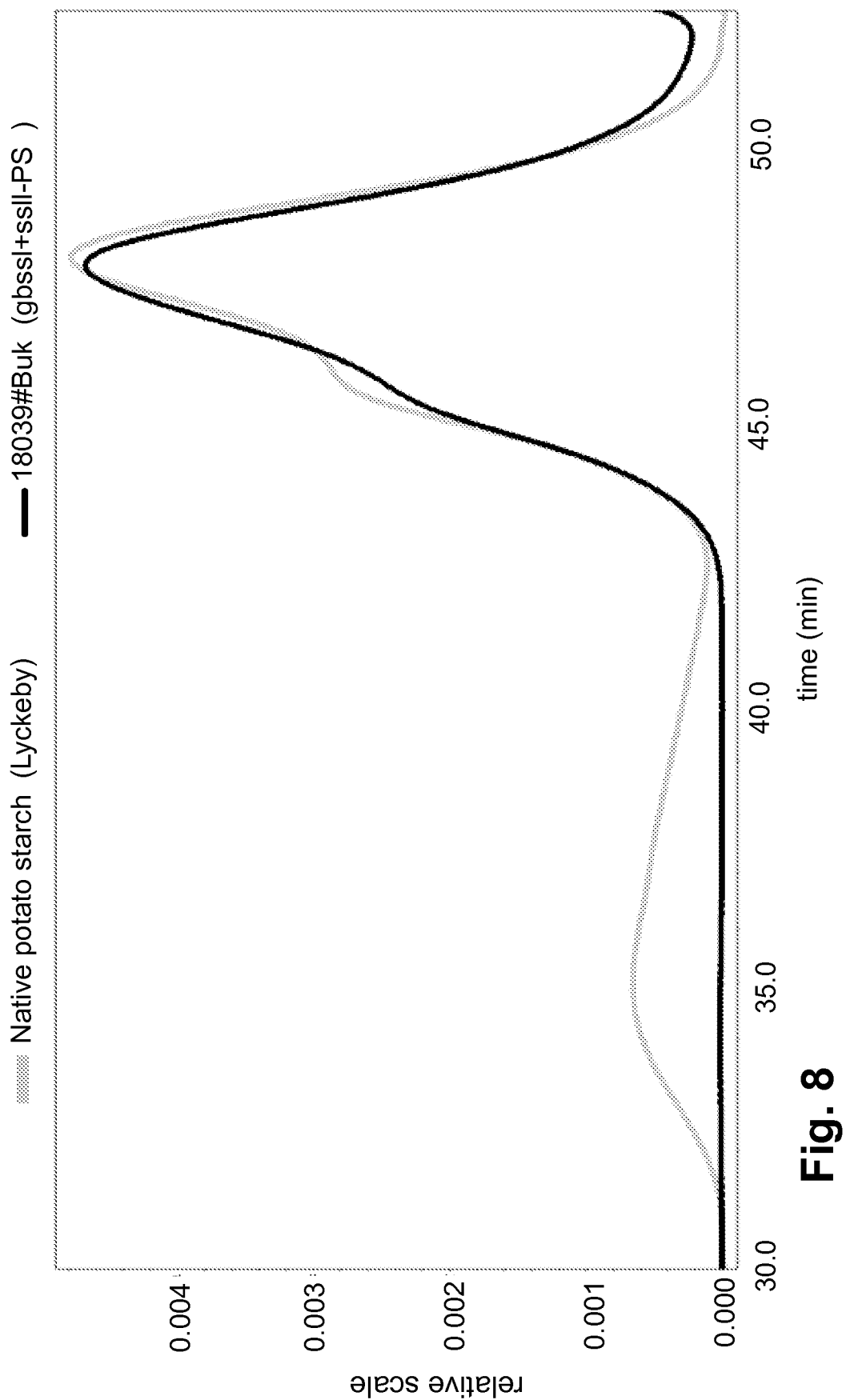
Figure 9:
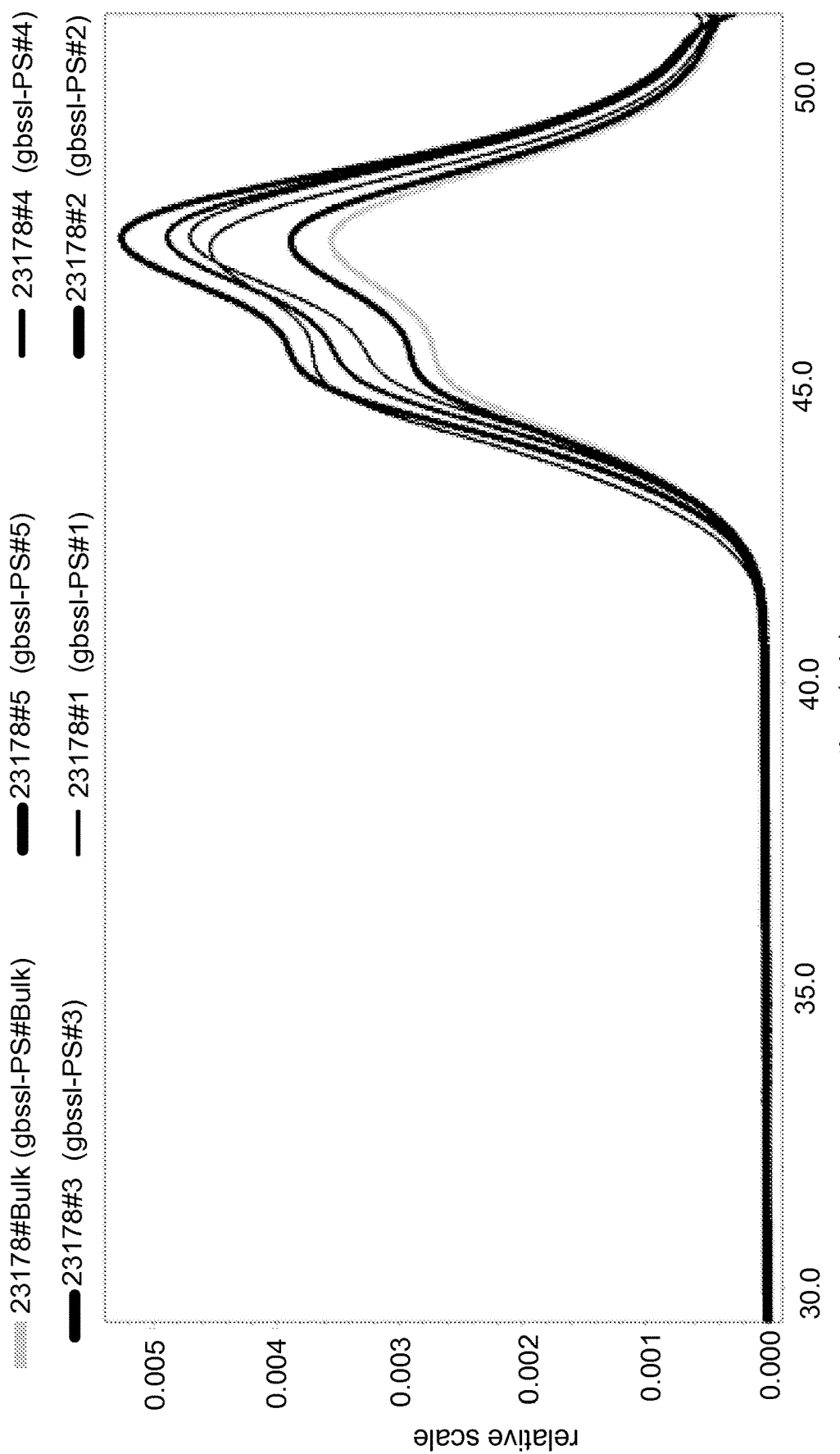

Starch was extracted from potato tubers from a number of individual mutated lines exemplified by lines 23178 (gbssI-PS), 18039 (gbssI/ssIII-PS), and 27031 (gbssI/ssIII-PS). In all cases, the bulked starch displayed more than 99% or 99.5% amylopectin. The result is shown in Table 3 and FIG. 7 for lines 27031 (gbssI/ssIII-PS) and 23178 (gbssI-PS) and in FIG. 8 for line 18039 (gbssI/ssIII-PS) together with traditional native potato starch. To investigate if any in between tuber variability could be found, starch isolated from five individual tubers of line 23178 (gbssI-PS) was assessed. The isolated starches of the five individual tubers all displayed more than 99.5% amylopectin. The results are shown in Table 3 and FIG. 9, where the results for line 23178 #1 (gbssI-PS #1), 23178 #2 (gbssI-PS #2), 23178 #3 (gbssI-PS #3), 23178 #4 (gbssI-PS #4), and 23178 #5 (gbssI-PS #5) are shown together with the bulk (rest of all potatoes) 23178 #Bulk (gbssI-PS #bulk). These results show that the present invention result in an amylopectin content as close to 100% as any method can determine. In addition, the results show that the present invention results in a stable amylopectin content as close to 100% as any method can determine, across all individual tubers from the same line.

TABLE 3

| Sample | 1. Amylose (%) | % of amylopectin | |
|---|---|---|---|
| | | 2. Long Amylopectin chains (%) | 3. Short Amylopectin chains (%) |
| Native potato starch (Lyckeby) | 21 | 32 | 68 |
| Commercial available waxy potato starch | <1 | 32 | 68 |
| Waxy Maize starch | <1 | 22 | 79 |
| BAP (Barley amylopectin starch) | <1 | 18 | 83 |
| 23178 #1 (gbssI-PS#1) | <1 | 38 | 62 |
| 23178 #2 (gbssI-PS#2) | <1 | 34 | 66 |
| 23178 #3 (gbssI-PS#3) | <1 | 33 | 67 |
| 23178 #4 (gbssI-PS#4) | <1 | 32 | 68 |
| 23178 #5 (gbssI-PS#5) | <1 | 35 | 65 |
| 23178#Bulk (gbssI-PS#bulk) | <1 | 35 | 65 |
| 18039 (gbssI + ssIII-PS) | <1 | 29 | 71 |
| 27031 (gbssI + ssIII-PS) | <1 | 27 | 74 |

LITERATURE REFERENCES

1. Zeeman, S. C., J. Kossmann, and A. M. Smith, Starch: Its Metabolism, Evolution, and Biotechnological Modification in Plants. Annual Review of Plant Biology, Vol 61, 2010. 61: p. 209-234.
2. Kossmann, J. and J. Lloyd, Understanding and influencing starch biochemistry. Critical Reviews in Biochemistry and Molecular Biology, 2000. 35(3): p. 141-196.
3. Jinek, M., et al., A Programmable Dual-RNA-Guided DNA Endonuclease in Adaptive Bacterial Immunity. Science, 2012. 337(6096): p. 816-821.
4. Chen, C., L. A. Fenk, and M. de Bono, Efficient genome editing in *Caenorhabditis elegans* by CRISPR-targeted homologous recombination. Nucleic Acids Research, 2013. 41(20).
5. Auer, T. O., et al., Highly efficient CRISPR/Cas9-mediated knock-in in zebrafish by homology-independent DNA repair. Genome Research, 2014. 24(1): p. 142-153.
6. Li, J.-F., et al., Multiplex and homologous recombination-mediated genome editing in *Arabidopsis* and *Nicotiana benthamiana* using guide RNA and Cas9. Nature Biotechnology, 2013. 31(8): p. 688-691.
7. Xie, K. and Y. Yang, RNA-Guided Genome Editing in Plants Using a CRISPRCas System. Molecular Plant, 2013. 6(6): p. 1975-1983.
8. Belhaj, K., et al., Plant genome editing made easy: targeted mutagenesis in model and crop plants using the CRISPR/Cas system. Plant Methods, 2013. 9.

9. Sun, X., et al., Targeted mutagenesis in soybean using the CRISPR-Cas9 system. Scientific Reports, 2015. 5.
10. Pattanayak, V., et al., High-throughput profiling of off-target DNA cleavage reveals RNA-programmed Cas9 nuclease specificity. Nature Biotechnology, 2013. 31(9): p. 839-+.
11. Hsu, P. D., et al., DNA targeting specificity of RNA-guided Cas9 nucleases. Nature Biotechnology, 2013. 31(9): p. 827-+.
12. Nicolia, A., et al., Targeted gene mutation in tetraploid potato through transient TALEN expression in protoplasts. Journal of Biotechnology, (0).

The invention claimed is:

1. Amylopectin potato starch, having more than 99.5% amylopectin, which has been extracted from a potato (*Solanum tuberosum*) in which the expression and/or activity of the GBSSI enzyme, of the SSIII enzyme, and of
the SSII enzyme has been completely eliminated,
wherein, the Amylopectin potato starch has a shorter amylopectin chain length compared to that of native amylopectin potato starch and a degree of branching of more than 5%.

2. The amylopectin potato starch according to claim 1, having less than 30% syneresis after 2 repeated freeze/thaw cycles according to a standardized freeze/thaw stability test.

3. The amylopectin starch according to claim 1, which has been purified after extraction from said potato by acid thinning, oxidation, acetylation, hydroxypropylation, cross-linking, sodiumoctenyl succinylation, aluminum-octenyl succinylation, succinylation, pyrodextrinization, enzymatic modifications, alkaline roasting, or cationic modification.

4. The amylopectin potato starch according to claim 1, which has been gelatinized and further dried to a dry content of more than 80% w/w dry matter (DM).

5. The amylopectin starch according to claim 1, wherein it has been degraded to a molecular weight of 100 000-1 000 000 Da with enzymatic modification or acid treatment, pyrodextrinization, oxidation degradation, or combinations thereof, or wherein it has been inhibited by alkaline roasting or a bleaching reaction with oxidizing agents.

6. The amylopectin potato starch of claim 1, consisting essentially of the amylopectin which has been extracted from the potato (*Solanum tuberosum*) in which the expression and/or activity of the GBSSI enzyme, of the SSIII enzyme, and of the SSII enzyme has been completely eliminated, wherein, the Amylopectin potato starch has a shorter amylopectin chain length compared to that of native amylopectin potato starch and a degree of branching of more than 5%.

7. The amylopectin potato starch according to claim 1, having less than 30% syneresis after 2 repeated freeze/thaw cycles according to a standardized freeze/thaw stability test.

8. The amylopectin potato starch of claim 1, wherein it has been gelatinized and further dried to a dry content of more than 85% w/w dry matter (DM).

9. The amylopectin potato starch of claim 1, wherein it has been gelatinized and further dried to a dry content of more than 90% w/w dry matter (DM).

10. The amylopectin starch according to claim 1, wherein it has been degraded to a molecular weight of 300 000-800 000 Da, with enzymatic modification or acid treatment, pyrodextrinization, oxidation degradation, or combinations thereof, or wherein it has been inhibited by alkaline roasting or a bleaching reaction with oxidizing agents.

11. The amylopectin starch according to claim 1, wherein it has been degraded to a molecular weight of 500 000-700 000 Da, with enzymatic modification or acid treatment, pyrodextrinization, oxidation degradation, or combinations thereof, or wherein it has been inhibited by alkaline roasting or a bleaching reaction with oxidizing agents.

\* \* \* \* \*

SEQUENCE LISTING

```
<160> NUMBER OF SEQ ID NOS: 96

<210> SEQ ID NO 1
<211> LENGTH: 20
<212> TYPE: DNA
<213> ORGANISM: Solanum tuberosum

<400> SEQUENCE: 1
gatattagaa tcacataggg                                                   20

<210> SEQ ID NO 2
<211> LENGTH: 20
<212> TYPE: DNA
<213> ORGANISM: Solanum tuberosum

<400> SEQUENCE: 2
tgttgacaag ggtgttgaat                                                   20

<210> SEQ ID NO 3
<211> LENGTH: 20
<212> TYPE: DNA
<213> ORGANISM: Solanum tuberosum

<400> SEQUENCE: 3
gctaccattg tttgtggaaa                                                   20

<210> SEQ ID NO 4
<211> LENGTH: 20
<212> TYPE: DNA
<213> ORGANISM: Solanum tuberosum

<400> SEQUENCE: 4
gacaagaaga tccctttgat                                                   20

<210> SEQ ID NO 5
<211> LENGTH: 20
<212> TYPE: DNA
<213> ORGANISM: Solanum tuberosum

<400> SEQUENCE: 5
gtgctaaaag gggtaagttg                                                   20

<210> SEQ ID NO 6
<211> LENGTH: 20
<212> TYPE: DNA
<213> ORGANISM: Solanum tuberosum

<400> SEQUENCE: 6
ggggtgccct ttcatcggcc                                                   20

<210> SEQ ID NO 7
<211> LENGTH: 20
<212> TYPE: DNA
<213> ORGANISM: Solanum tuberosum

<400> SEQUENCE: 7
gctccagtag agagcaaatg                                                   20
```

-continued

<210> SEQ ID NO 8
<211> LENGTH: 20
<212> TYPE: DNA
<213> ORGANISM: Solanum tuberosum

<400> SEQUENCE: 8
gaacatctga accaaatttc                                                   20

<210> SEQ ID NO 9
<211> LENGTH: 20
<212> TYPE: DNA
<213> ORGANISM: Solanum tuberosum

<400> SEQUENCE: 9
gaggtggcaa tggacccagg                                                   20

<210> SEQ ID NO 10
<211> LENGTH: 20
<212> TYPE: DNA
<213> ORGANISM: Solanum tuberosum

<400> SEQUENCE: 10
ggaaactaat gccagtagca                                                   20

<210> SEQ ID NO 11
<211> LENGTH: 29
<212> TYPE: DNA
<213> ORGANISM: Artificial sequence
<220> FEATURE:
<223> OTHER INFORMATION: primer

<400> SEQUENCE: 11
cctcttctca atcttcctga tgaattcag                                         29

<210> SEQ ID NO 12
<211> LENGTH: 29
<212> TYPE: DNA
<213> ORGANISM: Artificial sequence
<220> FEATURE:
<223> OTHER INFORMATION: primer

<400> SEQUENCE: 12
agagcctcct ttagtaaagg ttttgcgtc                                         29

<210> SEQ ID NO 13
<211> LENGTH: 22
<212> TYPE: DNA
<213> ORGANISM: Artificial sequence
<220> FEATURE:
<223> OTHER INFORMATION: primer

<400> SEQUENCE: 13
tgcttcacaa tccctaattc tc                                                22

<210> SEQ ID NO 14
<211> LENGTH: 22
<212> TYPE: DNA
<213> ORGANISM: Artificial sequence
<220> FEATURE:
<223> OTHER INFORMATION: primer

<400> SEQUENCE: 14
atccaaaagt gtctcttgac tg                                                22

```
<210> SEQ ID NO 15
<211> LENGTH: 23
<212> TYPE: DNA
<213> ORGANISM: Artificial sequence
<220> FEATURE:
<223> OTHER INFORMATION: primer

<400> SEQUENCE: 15
gcttagagaa gcggctatgc gtg                                              23

<210> SEQ ID NO 16
<211> LENGTH: 27
<212> TYPE: DNA
<213> ORGANISM: Artificial sequence
<220> FEATURE:
<223> OTHER INFORMATION: primer

<400> SEQUENCE: 16
tccatcatat atgcatccaa tggaacc                                          27

<210> SEQ ID NO 17
<211> LENGTH: 20
<212> TYPE: DNA
<213> ORGANISM: Artificial sequence
<220> FEATURE:
<223> OTHER INFORMATION: primer

<400> SEQUENCE: 17
actggatgaa ggctgggata                                                  20

<210> SEQ ID NO 18
<211> LENGTH: 20
<212> TYPE: DNA
<213> ORGANISM: Artificial sequence
<220> FEATURE:
<223> OTHER INFORMATION: primer

<400> SEQUENCE: 18
atttgtcagt cgctgggttc                                                  20

<210> SEQ ID NO 19
<211> LENGTH: 21
<212> TYPE: DNA
<213> ORGANISM: Artificial sequence
<220> FEATURE:
<223> OTHER INFORMATION: primer

<400> SEQUENCE: 19
aggaaccata ctctgactca c                                                21

<210> SEQ ID NO 20
<211> LENGTH: 19
<212> TYPE: DNA
<213> ORGANISM: Artificial sequence
<220> FEATURE:
<223> OTHER INFORMATION: primer

<400> SEQUENCE: 20
ttttgctcca aggaccaac                                                   19

<210> SEQ ID NO 21
<211> LENGTH: 21
<212> TYPE: DNA
<213> ORGANISM: Artificial sequence
<220> FEATURE:
<223> OTHER INFORMATION: primer
```

<400> SEQUENCE: 21
tctctataca ggtcatggac g                                          21

<210> SEQ ID NO 22
<211> LENGTH: 22
<212> TYPE: DNA
<213> ORGANISM: Artificial sequence
<220> FEATURE:
<223> OTHER INFORMATION: primer

<400> SEQUENCE: 22
gcagcaacaa gaatatctga ac                                         22

<210> SEQ ID NO 23
<211> LENGTH: 19
<212> TYPE: DNA
<213> ORGANISM: Artificial sequence
<220> FEATURE:
<223> OTHER INFORMATION: primer

<400> SEQUENCE: 23
tggaaatcag ttccacccc                                             19

<210> SEQ ID NO 24
<211> LENGTH: 22
<212> TYPE: DNA
<213> ORGANISM: Artificial sequence
<220> FEATURE:
<223> OTHER INFORMATION: primer

<400> SEQUENCE: 24
catggctaaa accttttgc tc                                          22

<210> SEQ ID NO 25
<211> LENGTH: 21
<212> TYPE: DNA
<213> ORGANISM: Artificial sequence
<220> FEATURE:
<223> OTHER INFORMATION: primer

<400> SEQUENCE: 25
cgataaaaat acaccgcctg c                                          21

<210> SEQ ID NO 26
<211> LENGTH: 19
<212> TYPE: DNA
<213> ORGANISM: Artificial sequence
<220> FEATURE:
<223> OTHER INFORMATION: primer

<400> SEQUENCE: 26
tctggaggga cattcaacg                                             19

<210> SEQ ID NO 27
<211> LENGTH: 20
<212> TYPE: DNA
<213> ORGANISM: Artificial sequence
<220> FEATURE:
<223> OTHER INFORMATION: primer

<400> SEQUENCE: 27
atccaagctg gaagcagtgt                                            20

<210> SEQ ID NO 28

<211> LENGTH: 20
<212> TYPE: DNA
<213> ORGANISM: Artificial sequence
<220> FEATURE:
<223> OTHER INFORMATION: primer

<400> SEQUENCE: 28
gacatgggtg ccattttcag                                              20

<210> SEQ ID NO 29
<211> LENGTH: 22
<212> TYPE: DNA
<213> ORGANISM: Artificial sequence
<220> FEATURE:
<223> OTHER INFORMATION: primer

<400> SEQUENCE: 29
tgatgacaag gatgctgtaa ag                                           22

<210> SEQ ID NO 30
<211> LENGTH: 21
<212> TYPE: DNA
<213> ORGANISM: Artificial sequence
<220> FEATURE:
<223> OTHER INFORMATION: primer

<400> SEQUENCE: 30
tcaacatcca cctgcaatat c                                            21

<210> SEQ ID NO 31
<211> LENGTH: 38
<212> TYPE: DNA
<213> ORGANISM: Solanum tuberosum

<400> SEQUENCE: 31
gggatattag aatcacatag ggtggttaca gtgagccc                          38

<210> SEQ ID NO 32
<211> LENGTH: 42
<212> TYPE: DNA
<213> ORGANISM: Solanum tuberosum

<400> SEQUENCE: 32
ttgtctctgc tgttgacaag ggtgttgaat tggacagtgt cc                     42

<210> SEQ ID NO 33
<211> LENGTH: 44
<212> TYPE: DNA
<213> ORGANISM: Solanum tuberosum

<400> SEQUENCE: 33
ctggatgctc agctaccatt gtttgtaaag ggaatgaact tgat                   44

<210> SEQ ID NO 34
<211> LENGTH: 38
<212> TYPE: DNA
<213> ORGANISM: Solanum tuberosum

<400> SEQUENCE: 34
cctgttgaca agaagatccc tttgattggc ttcatcgg                          38

<210> SEQ ID NO 35
<211> LENGTH: 38
<212> TYPE: DNA
<213> ORGANISM: Solanum tuberosum

<400> SEQUENCE: 35
ttttgggcct aagtgctaaa aggggtaagt tggggtgg                                    38

<210> SEQ ID NO 36
<211> LENGTH: 32
<212> TYPE: DNA
<213> ORGANISM: Solanum tuberosum

<400> SEQUENCE: 36
gggggtgccc tttcatcggc caggtccctt tt                                          32

<210> SEQ ID NO 37
<211> LENGTH: 38
<212> TYPE: DNA
<213> ORGANISM: Solanum tuberosum

<400> SEQUENCE: 37
cagcgattaa atgaacatct gaaccaaatt tcaggttt                                    38

<210> SEQ ID NO 38
<211> LENGTH: 38
<212> TYPE: DNA
<213> ORGANISM: Solanum tuberosum

<400> SEQUENCE: 38
ggcaacattt tctgaggtgg caatggaccc aggcggtg                                    38

<210> SEQ ID NO 39
<211> LENGTH: 37
<212> TYPE: DNA
<213> ORGANISM: Artificial sequence
<220> FEATURE:
<223> OTHER INFORMATION: primer

<400> SEQUENCE: 39
taatacgact cactatagac aagaagatcc ctttgat                                     37

<210> SEQ ID NO 40
<211> LENGTH: 34
<212> TYPE: DNA
<213> ORGANISM: Artificial sequence
<220> FEATURE:
<223> OTHER INFORMATION: primer

<400> SEQUENCE: 40
ttctagctct aaaacatcaa agggatcttc ttgt                                        34

<210> SEQ ID NO 41
<211> LENGTH: 37
<212> TYPE: DNA
<213> ORGANISM: Artificial sequence
<220> FEATURE:
<223> OTHER INFORMATION: primer

<400> SEQUENCE: 41
taatacgact cactatagag gtggcaatgg acccagg                                     37

<210> SEQ ID NO 42
<211> LENGTH: 34
<212> TYPE: DNA
<213> ORGANISM: Artificial sequence
<220> FEATURE:
<223> OTHER INFORMATION: primer

```
<400> SEQUENCE: 42
ttctagctct aaaaccctgg gtccattgcc acct                                34

<210> SEQ ID NO 43
<211> LENGTH: 37
<212> TYPE: DNA
<213> ORGANISM: Artificial sequence
<220> FEATURE:
<223> OTHER INFORMATION: primer

<400> SEQUENCE: 43
taatacgact cactatagct ccagtagaga gcaaatg                             37

<210> SEQ ID NO 44
<211> LENGTH: 34
<212> TYPE: DNA
<213> ORGANISM: Artificial sequence
<220> FEATURE:
<223> OTHER INFORMATION: primer

<400> SEQUENCE: 44
ttctagctct aaaaccattt gctctctact ggag                                34

<210> SEQ ID NO 45
<211> LENGTH: 244
<212> TYPE: DNA
<213> ORGANISM: Solanum tuberosum

<400> SEQUENCE: 45
atatgagaag cctgttaagg gtaggaaaat caactggatg aaggctggga tattagaatc    60
acatagggtg gttacagtga gcccatacta tgcccaagaa cttgtctctg ctgttgacaa   120
gggtgttgaa ttggacagtg tccttcgtaa gacttgcata actgggattg tgaatggcat   180
ggatacacaa gagtggaacc cagcgactga caaatacaca gatgtcaaat acgatataac   240
cact                                                                244

<210> SEQ ID NO 46
<211> LENGTH: 244
<212> TYPE: DNA
<213> ORGANISM: Solanum tuberosum

<400> SEQUENCE: 46
atatgagaag cctgttaagg gtaggaaaat caactggatg aaggctggga tattagaatc    60
gcatagggtg gttacagtga gcccatacta tgcccaagaa cttgtctctg ctgttgacaa   120
gggtgttgaa ttggacagtg tccttcgtaa gacttgcata actgggattg tgaatggcat   180
ggatacacaa gagtggaacc cagcgactga caaatacaca gatgtcaaat acgatataac   240
cact                                                                244

<210> SEQ ID NO 47
<211> LENGTH: 252
<212> TYPE: DNA
<213> ORGANISM: Solanum tuberosum

<400> SEQUENCE: 47
atggagaatt ccattcttct tcatagtgga aatcagttcc accccaactt accccttta     60 gcacttaggc ccaaaaaatt atctctaatt catggctcca gtagagagca aatgtggagg   120
atcaagcgcg ttaagcaac aggtgaaaat tctggggaag ctgcaagtgc tgatgaatcg    180
aatgatgcct tacaggttac aattgaaaag agcaaaaagg ttttagccat gcaacaggac   240
```

```
ctacttcaac ag                                                                  252

<210> SEQ ID NO 48
<211> LENGTH: 252
<212> TYPE: DNA
<213> ORGANISM: Solanum tuberosum

<400> SEQUENCE: 48
atggagaatt ccattcttct tcatagtgga aatcagttcc accccaactt acccctttc    60 gcacttaggc ccaaaaaatt atctctaatt catggctcca gtagagagca aatgtggagg   120
atcaagcgcg ttaaagcaac aggtgaaaat tctggggaag ctgcaagggc tgatgaatcg   180
aatgatgcct tacaggttac aattgaaaag agcaaaaagg ttttagccat gcaacaggac   240
ctacttcaac ag                                                       252

<210> SEQ ID NO 49
<211> LENGTH: 252
<212> TYPE: DNA
<213> ORGANISM: Solanum tuberosum

<400> SEQUENCE: 49
atggagaatt ccattcttct tcatagtgga aatcagttcc accccaactt accccttta    60 gcacttaggc ccaaaaaatt atctctaatt catggctcca gtagagagca aatgtggagg   120
atcaagcgcg ttaaagcaac aggtgaaaat tctggggaag ctgcaagggc tgatgaatcg   180
aatgatgcct tacaggttac aattgaaaag agcaaaaagg ttttagccat gcaacaggac   240
ctacttcaac ag                                                       252

<210> SEQ ID NO 50
<211> LENGTH: 252
<212> TYPE: DNA
<213> ORGANISM: Solanum tuberosum
<220> FEATURE:
<221> NAME/KEY: misc_feature
<222> LOCATION: (168)..(168)
<223> OTHER INFORMATION: n is a, c, g, or t

<400> SEQUENCE: 50
atggagaatt ccattcttct tcatagtgga aatcagttcc accccaactt accccttta    60 gcacttaggc ccaaaaaatt atctctaatt catggctcca gtagagagca aatgtggagg   120
atcaagcgcg ttaaagcaac aggtgaaaat tctggggaag ctgcaagngc tgatgaatcg   180
aatgatgcct tacaggttac aattgaaaag agcaaaaagg ttttagccat gcaacaggac   240
ctacttcaac ag                                                       252

<210> SEQ ID NO 51
<211> LENGTH: 271
<212> TYPE: DNA
<213> ORGANISM: Solanum tuberosum

<400> SEQUENCE: 51
gttgaaaaaa cagcacttct gaaaactgaa acaaaggaaa gaactatgaa atcattttta    60
ctgtctcaga agcatgtagt atatactgag cctcttgata tccaagctgg aagcagtgtc   120
acagtttact ataatcccgc caatacagta cttaatggta aacctgaaat ttggttcaga   180
tgttcattta atcgctggac tcaccgcctg ggtccattgc cacctcagaa aatgtcgcct   240
gctgaaaatg gcacccatgt cagagcaact g                                  271
```

<210> SEQ ID NO 52
<211> LENGTH: 271
<212> TYPE: DNA
<213> ORGANISM: Solanum tuberosum

<400> SEQUENCE: 52
gttgaaaaaa cagcacttct gaaagctgaa acaaaggaaa gaactatgaa atcattttta     60
ctgtctcaga agcatgtagt atatactgag cctcttgata tccaagctgg aagcagcgtc    120
acagtttact ataatcccgc caatacagta cttaatggta aacctgaaat ttggttcaga    180
tgttcattta atcgctggac tcaccgcctg ggtccattgc cacctcagaa aatgtcgcct    240
gctgaaaatg gcacccatgt cagagcaact g                                   271

<210> SEQ ID NO 53
<211> LENGTH: 271
<212> TYPE: DNA
<213> ORGANISM: Solanum tuberosum

<400> SEQUENCE: 53
gttgaaaaaa cagcacttct gaaaactgaa acaaaggaaa gaactatgaa atcattttta     60
ctgtctcaga agcatgtagt atatactgag cctcttgata tccaagctgg aagcagcgtc    120
acagtttact ataatcccgc caatacagta cttaatggta aacctgaaat ttggttcaga    180
tgttcattta atcgctggac tcaccgcctg ggtccattgc cacctcagaa aatgtcgcct    240
gctgaaaatg gcacccatgt cagagcaact g                                   271

<210> SEQ ID NO 54
<211> LENGTH: 271
<212> TYPE: DNA
<213> ORGANISM: Solanum tuberosum
<220> FEATURE:
<221> NAME/KEY: misc_feature
<222> LOCATION: (117)..(117)
<223> OTHER INFORMATION: n is a, c, g, or t

<400> SEQUENCE: 54
gttgaaaaaa cagcacttct gaaaactgaa acaaaggaaa gaactatgaa atcattttta     60
ctgtctcaga agcatgtagt atatactgag cctcttgata tccaagctgg aagcagngtc    120
acagtttact ataatcccgc caatacagta cttaatggta aacctgaaat ttggttcaga    180
tgttcattta atcgctggac tcaccgcctg ggtccattgc cacctcagaa aatgtcgcct    240
gctgaaaatg gcacccatgt cagagcaact g                                   271

<210> SEQ ID NO 55
<211> LENGTH: 37
<212> TYPE: DNA
<213> ORGANISM: Solanum tuberosum

<400> SEQUENCE: 55
gggatattag aatcacatgg gtggttacag tgagccc                              37

<210> SEQ ID NO 56
<211> LENGTH: 32
<212> TYPE: DNA
<213> ORGANISM: Solanum tuberosum

<400> SEQUENCE: 56
gggatattag aatgggtggt tacagtgagc cc                                   32

```
<210> SEQ ID NO 57
<211> LENGTH: 37
<212> TYPE: DNA
<213> ORGANISM: Solanum tuberosum

<400> SEQUENCE: 57
gggatattag aatcacatgg gtggttacag tgagccc                              37

<210> SEQ ID NO 58
<211> LENGTH: 31
<212> TYPE: DNA
<213> ORGANISM: Solanum tuberosum

<400> SEQUENCE: 58
gggatattag aagggtggtt acagtgagcc c                                    31

<210> SEQ ID NO 59
<211> LENGTH: 34
<212> TYPE: DNA
<213> ORGANISM: Solanum tuberosum

<400> SEQUENCE: 59
gggatattag aatcagggtg gttacagtga gccc                                 34

<210> SEQ ID NO 60
<211> LENGTH: 33
<212> TYPE: DNA
<213> ORGANISM: Solanum tuberosum

<400> SEQUENCE: 60
gggatattag aatcgggtgg ttacagtgag ccc                                  33

<210> SEQ ID NO 61
<211> LENGTH: 37
<212> TYPE: DNA
<213> ORGANISM: Solanum tuberosum

<400> SEQUENCE: 61
gggatattag aatcacatgg gtggttacag tgagccc                              37

<210> SEQ ID NO 62
<211> LENGTH: 36
<212> TYPE: DNA
<213> ORGANISM: Solanum tuberosum

<400> SEQUENCE: 62
gggatattag aatcacaggg tggttacagt gagccc                               36

<210> SEQ ID NO 63
<211> LENGTH: 28
<212> TYPE: DNA
<213> ORGANISM: Solanum tuberosum

<400> SEQUENCE: 63
gggatattag ggtggttaca gtgagccc                                        28

<210> SEQ ID NO 64
<211> LENGTH: 35
<212> TYPE: DNA
<213> ORGANISM: Solanum tuberosum

<400> SEQUENCE: 64
gggatattag aatcaagggt ggttacagtg agccc                                35
```

<210> SEQ ID NO 65
<211> LENGTH: 37
<212> TYPE: DNA
<213> ORGANISM: Solanum tuberosum

<400> SEQUENCE: 65
gggatattag aatcacatgg gtggttacag tgagccc                    37

<210> SEQ ID NO 66
<211> LENGTH: 38
<212> TYPE: DNA
<213> ORGANISM: Solanum tubeosum

<400> SEQUENCE: 66
ttgtctctgc tgttgacaag ggtaattgga cagtgtcc                   38

<210> SEQ ID NO 67
<211> LENGTH: 43
<212> TYPE: DNA
<213> ORGANISM: Solanum tuberosum

<400> SEQUENCE: 67
ttgtctctgc tgttgacaag ggtgttgaaa ttggacagtg tcc             43

<210> SEQ ID NO 68
<211> LENGTH: 38
<212> TYPE: DNA
<213> ORGANISM: Solanum tuberosum

<400> SEQUENCE: 68
ttgtctctgc tgttgacaag ggtgattgga cagtgtcc                   38

<210> SEQ ID NO 69
<211> LENGTH: 41
<212> TYPE: DNA
<213> ORGANISM: Solanum tuberosum

<400> SEQUENCE: 69
ttgtctctgc tgttgacaag ggtgttaatt ggacagtgtc c               41

<210> SEQ ID NO 70
<211> LENGTH: 41
<212> TYPE: DNA
<213> ORGANISM: Solanum tuberosum

<400> SEQUENCE: 70
ttgtctctgc tgttgacaag ggtgttaatt ggacagtgtc c               41

<210> SEQ ID NO 71
<211> LENGTH: 40
<212> TYPE: DNA
<213> ORGANISM: Solanum tuberosum

<400> SEQUENCE: 71
ttgtctctgc tgttgacaag ggtgttgttg gacagtgtcc                 40

<210> SEQ ID NO 72
<211> LENGTH: 34
<212> TYPE: DNA
<213> ORGANISM: Solanum tuberosum

<400> SEQUENCE: 72
ttgtctctgc tgttgacaaa attggacagt gtcc                       34

<210> SEQ ID NO 73
<211> LENGTH: 36
<212> TYPE: DNA
<213> ORGANISM: Solanum tuberosum

<400> SEQUENCE: 73
cctgttgaca agaagatccc tgattggctt catcgg                                    36

<210> SEQ ID NO 74
<211> LENGTH: 39
<212> TYPE: DNA
<213> ORGANISM: Solanum tuberosum

<400> SEQUENCE: 74
cctgttgaca agaagatccc tttagattgg cttcatcgg                                 39

<210> SEQ ID NO 75
<211> LENGTH: 30
<212> TYPE: DNA
<213> ORGANISM: Solanum tuberosum

<400> SEQUENCE: 75
cctgttgaca agaaggattg gcttcatcgg                                           30

<210> SEQ ID NO 76
<211> LENGTH: 34
<212> TYPE: DNA
<213> ORGANISM: Solanum tuberosum

<400> SEQUENCE: 76
cctgttgaca agaagatccg attggcttca tcgg                                      34

<210> SEQ ID NO 77
<211> LENGTH: 39
<212> TYPE: DNA
<213> ORGANISM: Solanum tuberosum

<400> SEQUENCE: 77
cctgttgaca agaagatccc ttttgattgg cttcatcgg                                 39

<210> SEQ ID NO 78
<211> LENGTH: 29
<212> TYPE: DNA
<213> ORGANISM: Solanum tuberosum

<400> SEQUENCE: 78
cctgttgaca agaagattgg cttcatcgg                                            29

<210> SEQ ID NO 79
<211> LENGTH: 36
<212> TYPE: DNA
<213> ORGANISM: Solanum tuberosum

<400> SEQUENCE: 79
cctgttgaca agaagatccc tgattggctt catcgg                                    36

<210> SEQ ID NO 80
<211> LENGTH: 28
<212> TYPE: DNA
<213> ORGANISM: Solanum tuberosum

<400> SEQUENCE: 80
cctgttgaca agaagatccc ttcatcgg        28

<210> SEQ ID NO 81
<211> LENGTH: 36
<212> TYPE: DNA
<213> ORGANISM: Solanum tuberosum

<400> SEQUENCE: 81
cctgttgaca agaagatccc tgattggctt catcgg        36

<210> SEQ ID NO 82
<211> LENGTH: 21
<212> TYPE: DNA
<213> ORGANISM: Solanum tuberosum

<400> SEQUENCE: 82
cctgttgatt ggcttcatcg g        21

<210> SEQ ID NO 83
<211> LENGTH: 35
<212> TYPE: DNA
<213> ORGANISM: Solanum tuberosum

<400> SEQUENCE: 83
cctgttgaca agaagatccc tattggcttc atcgg        35

<210> SEQ ID NO 84
<211> LENGTH: 39
<212> TYPE: DNA
<213> ORGANISM: Solanum tuberosum

<400> SEQUENCE: 84
cctgttgaca agaagatccc ttttgattgg cttcatcgg        39

<210> SEQ ID NO 85
<211> LENGTH: 42
<212> TYPE: DNA
<213> ORGANISM: Solanum tuberosum

<400> SEQUENCE: 85
ctggatgctc agctaccatt gtttaaaggg aatgaacttg at        42

<210> SEQ ID NO 86
<211> LENGTH: 36
<212> TYPE: DNA
<213> ORGANISM: Solanum tuberosum

<400> SEQUENCE: 86
ttttgggcct aagtgctaaa aggggtattg gggtgg        36

<210> SEQ ID NO 87
<211> LENGTH: 37
<212> TYPE: DNA
<213> ORGANISM: Solanum tuberosum

<400> SEQUENCE: 87
ttttgggcct aagtgctaaa aggggtaatt ggggtgg        37

<210> SEQ ID NO 88
<211> LENGTH: 39
<212> TYPE: DNA
<213> ORGANISM: Solanum tuberosum

<400> SEQUENCE: 88
ttttgggcct aagtgctaaa aggggtaagt ttggggtgg                              39

<210> SEQ ID NO 89
<211> LENGTH: 35
<212> TYPE: DNA
<213> ORGANISM: Solanum tuberosum

<400> SEQUENCE: 89
ttttgggcct aagtgctaaa aggggtttgg ggtgg                                 35

<210> SEQ ID NO 90
<211> LENGTH: 33
<212> TYPE: DNA
<213> ORGANISM: Solanum tuberosum

<400> SEQUENCE: 90
gggggtgccc tttcatcgtg ccaggtccct ttt                                   33

<210> SEQ ID NO 91
<211> LENGTH: 36
<212> TYPE: DNA
<213> ORGANISM: Solanum tuberosum

<400> SEQUENCE: 91
cagcgattaa atgaacatct gaaccaattc aggttt                                36

<210> SEQ ID NO 92
<211> LENGTH: 36
<212> TYPE: DNA
<213> ORGANISM: Solanum tuberosum

<400> SEQUENCE: 92
ggcgacattt tctgaggtgg caatggacag gcggtg                                36

<210> SEQ ID NO 93
<211> LENGTH: 33
<212> TYPE: DNA
<213> ORGANISM: Solanum tuberosum

<400> SEQUENCE: 93
ggcgacattt tctgaggtgg caatgaggcg gtg                                   33

<210> SEQ ID NO 94
<211> LENGTH: 36
<212> TYPE: DNA
<213> ORGANISM: Solanum tuberosum

<400> SEQUENCE: 94
ggcgacattt tctgaggtgg caatggacag gcggtg                                36

<210> SEQ ID NO 95
<211> LENGTH: 34
<212> TYPE: DNA
<213> ORGANISM: Solanum tuberosum

<400> SEQUENCE: 95
ggcgacattt tctgaggtgg caatggaggc ggtg                                  34

<210> SEQ ID NO 96
<211> LENGTH: 28
<212> TYPE: DNA
<213> ORGANISM: Solanum tuberosum

```
<400> SEQUENCE: 96
ggcgacattt tctgaggtgg aggcggtg                                                    28
```